(12) United States Patent
Teoh et al.

(10) Patent No.: US 8,207,402 B2
(45) Date of Patent: Jun. 26, 2012

(54) NUCLEOTIDE SEQUENCES ENCODING ENZYMES IN BIOSYNTHESIS OF DIHYDROARTEMISINIC ACID

(75) Inventors: Keat (Thomas) H. Teoh, Jonesboro, AR (US); Darwin R. Reed, Saskatoon (CA); Devin R. Polichuk, Saskatoon (CA); Patrick S. Covello, Saskatoon (CA)

(73) Assignee: National Research Council of Canada, Ottawa, Ontario (CA)

( * ) Notice: Subject to any disclaimer, the term of this patent is extended or adjusted under 35 U.S.C. 154(b) by 703 days.

(21) Appl. No.: 12/225,556

(22) PCT Filed: Apr. 4, 2007

(86) PCT No.: PCT/CA2007/000614
§ 371 (c)(1),
(2), (4) Date: Mar. 19, 2009

(87) PCT Pub. No.: WO2007/112596
PCT Pub. Date: Oct. 11, 2007

(65) Prior Publication Data
US 2009/0265804 A1    Oct. 22, 2009

Related U.S. Application Data

(60) Provisional application No. 60/789,138, filed on Apr. 5, 2006, provisional application No. 60/857,503, filed on Nov. 8, 2006.

(51) Int. Cl.
*C12N 15/29* (2006.01)
*C12N 15/52* (2006.01)
*C12N 15/82* (2006.01)
(52) U.S. Cl. .......... 800/298; 800/266; 435/41; 536/23.6
(58) Field of Classification Search ................ 800/298, 800/266; 536/23.6; 435/41
See application file for complete search history.

(56) References Cited

U.S. PATENT DOCUMENTS

| 4,952,603 | A | 8/1990 | Eferlay et al. |
| 6,393,763 | B1 | 5/2002 | Kumar |
| 7,091,027 | B1 | 8/2006 | Wallaart et al. |
| 7,172,886 | B2 | 2/2007 | Keasling et al. |
| 2005/0108791 | A1 | 5/2005 | Edgerton |

FOREIGN PATENT DOCUMENTS

| EP | 1 586 652 | 10/2005 |
| EP | 09 17 6132 | 5/2010 |
| WO | WO 00/12725 | 3/2000 |
| WO | WO 2004/101755 A2 | 11/2004 |

OTHER PUBLICATIONS

Jin, Z. et al. Genbank Accession GI: 48431272, Jun. 13, 2004.*
Altschul, S. F., Gish, W., Miller, W., Myers, E., & Lipman, D. J. 1990, "Basic local alignment search tool", Journal of Molecular Biology, vol. 215, pp. 403-410.
Bagge, M., Xia, X., & Lubberstedt, T. 2007, "Functional markers in wheat", Curr. Opin. Plant Biol., vol. 10, No. 2, pp. 211-216.
Bertea, C. M., Freije, J. R., van der, W. H., Verstappen, F. W., Perk, L., Marquez, V., de Kraker, J. W., Posthumus, M. A., Jansen, B. J., de Groot, A., Franssen, M. C., & Bouwmeester, H. J. 2005, "Identification of intermediates and enzymes involved in the early steps of artemisinin biosynthesis in *Artemisia annua*", Planta Med., vol. 71, No. 1, pp. 40-47.
Bouwmeester, H. J., Wallaart, E. T., Janssen, M. H., van Loo, B., Jansen, B. J. M., Posthumus, M. A., Schmidt, C. O.; De Kraker, J.-W., Konig, W. A., & Franssen, M. C. R. 1999, "Amorpha-4,11-diene synthase catalyses the first probable step in artemisinin biosynthesis", Phytochemistry, vol. 52, pp. 843-854.
Cahoon, E. B., Carlson, T. J., Ripp, K. G., Schweiger, B. J., Cook, G. A., Hall, S. E., & Kinney, A. J. 1999, "Biosynthetic origin of conjugated double bonds: production of fatty acid components of high-value drying oils in transgenic soybean embryos", Proceedings of the National Academy of Sciences (U.S.A.), vol. 96, pp. 12935-12940.
Chang, Y. J., Song, S. H., Park, S. H., & Kim, S. U. 2000, "Amorpha-4,11-diene synthase of *Artemisia annua*: cDNA isolation and bacterial expression of a terpene synthase involved in artemisinin biosynthesis", Archives of Biochemistry and Biophysics, vol. 383, No. 2, pp. 178-184.
Chou, H.-H. & Holmes, M. H. 2001, "DNA sequence quality trimming and vector removal", Bioinformatics, vol. 17, pp. 1093-1104.
Comai, L. & Henikoff, S. 2006, "TILLING: practical single-nucleotide mutation discovery", Plant J., vol. 45, No. 4, pp. 684-694.
Corey, E.J., & Suggs, J.W. 1975, "Pyridinium Chlorochromate: An efficient reagent for oxidation of primary and secondary alcohols to carbonyl compounds", Tetrahedron Lett. vol. 31, pp. 2647-2650.
Duke, M. V., Paul, R. N., Elsohly, H. N., Sturtz, G., & Duke, S. O. 1994, "Localization of artemisinin and artemisitene in foliar tisuues of glanded and glandless biotypes of *Artemisia annua*", Int.J.Plant Sci., vol. 155, pp. 365-372.
Duke, S. O. & Paul, R. N. 1993, "Development and fine structure of the glandular trichomes of *Artemisia annua*L.", Int.J.Plant Sci., vol. 154, pp. 107-118. Ewing, B., Hillier, L., Wendl, M. C., & Green, P. 1998, "Base-calling of automated sequencer traces using phred I. acurracy assessment", Genome Res., vol. 8, pp. 175-185.
Gang, D. R., Wang, J., Dudareva, N., Nam, K. H., Simon, J. E., Lewinsohn, E., & Pichersky, E. 2001, "An investigation of the storage and biosynthesis of phenylpropenes in sweet basil", Plant Physiol, vol. 125, No. 2, pp. 539-555.
Gupta, S. K., Singh, P., Bajpai, P., Ram, G., Singh, D., Gupta, M. M., Jain, D. C., Khanuja, S. P., & Kumar, S. 2002, "Morphogenetic variation for artemisinin and volatile oil in *Atemisia annua*", Ind Crops Products, vol. 16, pp. 217-224.
Henikoff S, Till BJ, Comai L (2004). "TILLING. Traditional mutagenesis meets functional genomics", Plant Physiol 135:630-6.

(Continued)

*Primary Examiner* — Russell Kallis
(74) *Attorney, Agent, or Firm* — National Research Council of Canada

(57) ABSTRACT

Isolated nucleic acid molecules cloned from *Artemisia annua* encode artemisinic aldehyde double bond reductase and artemisinic/dihydroartemisinic aldehyde dehydrogenase. Artemisinic aldehyde double bond reductase enzymatically reduces artemisinic aldehyde to dihydroartemisinic aldehyde. Artemisinic/dihydroartemisinic aldehyde dehydrogenase enzymatically oxidizes dihydroartemisinic aldehyde to dihydroartemisinic acid and artemisinic aldehyde to artemisinic acid. The nucleic acid molecules, and the enzymes encoded thereby, may be used in processes to produce dihydroartemsinic aldehyde, dihydroartemisinic acid or artemisinic acid in a host cell. Dihydroartemisinic acid is a late precursor to the a antimalarial compound artemisinin.

10 Claims, 7 Drawing Sheets

OTHER PUBLICATIONS

Jung, M., Lee, K., & Jung, H. 2001, "First synthesis of (+)-deoxyartemisitene and its novel C-11 derivatives", Tetrahedron Lett, vol. 42, pp. 3997-4000.

Konieczny, A., Ausubel, F.M. 1993, A procedure for mapping *Arabidopsis*mutations using co-dominant ecotype-specific PCR-based markers:, The Plant Journal 4 (2), 403-410.

Lange, B. M., Wildung, M. R., Stauber, E. J., Sanchez, C., Pouchnik, D., & Croteau, R. 2000, "Probing essential oil biosynthesis and secretion by functional evaluation of expressed sequence tags from mint glandular trichomes", Proc. Natl. Acad. Sci. U.S.A, vol. 97, No. 6, pp. 2934-2939.

Logemann, J., Schell, J., & Willmitazer, L. 1987, "Improved Method for the isolation of RNA from plant tissues", Analytical Biochemistry, vol. 163, pp. 16-20.

Martin, V. J., Pitera, D. J., Withers, S. T., Newman, J. D., & Keasling, J. D. 2003, "Engineering a mevalonate pathway in *Escherichia coli* for production of terpenoids", Nat.Biotechnol., vol. 21, No. 7, pp. 796-802.

Miller, R. T., Christoffels, A. G., Gopalakrishnan, C., Burke, J., Ptitsyn, A. A., Broveak, T. R., & Hide, W. A. 1999, "A comprehensive approach to clustering of expressed human gene sequence: the sequence tag alignment and consensus knowledge base", Genome Res., vol. 9, No. 11, pp. 1143-1155.

O'Neill, P. M. 2005, "The therapeutic potential of semi-synthetic artemisinin and synthetic endoperoxide antimalarial agents", Expert. Opin.Investig.Drugs, vol. 14, No. 9, pp. 1117-1128.

Pfaff, T. & Kahl, G. 2003, "Mapping of gene-specific markers on the genetic map of chickpea (*Cicer arietinum* L.)", Mol. Genet. Genonmics, vol. 269, No. 2, pp. 243-251.

Rathore, D., McCutchan, T.F., Sullivan, M., & Kumar, S. 2005,"Antimalarial drugs: current status and new developments", Expert.Opin.Investig.Drugs, vol. 14, No. 7, pp. 871-883.

Ringer, K. L., McConkey, M. E., Davis, E. M., Rushing, G. W., & Croteau, R. 2003, "Monoterpene double-bond reductases of the (−)-menthol biosynthetic pathway: isolation and characterization of cDNAs encoding (−)-isopiperitenone reductase and (+)-pulegone reductase of peppermint", Arch.Biochem.Biophys., vol. 418, pp. 80-92.

Ro, D.K., Paradise, E.M., Ouellet, M., Fisher, K.J., Newman, K.L., Ndungu, J.M., Ho, K.A., Eachus, R.A., Ham, T.S., Kirby, J., Chang, M.C., Withers, S.T., Shiba, Y., Sarpong, R., & Keasling, J.D. 2006, "Production of the antimalarial drug precursor artemisinic acid in engineered yeast", Nature, vol. 440, No. 7068, pp. 940-943.

Robert, A., Coppel, Y., & Meunier, B. 2002, "Alkylation of heme by the antimalarial drug artemisinin", Chem.Commun.(Camb.) No. 5, pp. 414-415.

Sandal, N., Krusell, L., Tadutoiu, S., Olbryt, M., Pedrosa, A., Stracke, S., Sato, S., Kato, T., Tabata, S., Parniske, M., Bachmair, A., Ketelsen, T., & Stougaard, J. 2002, "A genentic linkage map of the model legume *Lotus japonicus* and strategies for fast mapping of new loci", Genetics, vol. 161, No. 4, pp. 1673-1683.

Schwikkard, S. & van Heerden, F. R. 2002, "Antimalarial activity of plant metabolites", Natural Product Reports, vol. 19, No. 6, pp. 675-692.

Slade, A.J. & Knauf, V.C. 2005, "TILLING moves beyond functional genomics into crop improvement", Transgenic Res., vol. 14, No. 2, pp. 109-115.

Stone, R.T., Grosse, W.M., Casas, E., Smith, T.P., Keele, J.W., & Bennett, G.L. 2002, "Use of bovine EST data and human genomic sequences to map 100 gene-specific bovine markers", Mammalian Genome, vol. 13, No. 4, pp. 211-215.

Sy, L.-K. & Brown, G.D. 2002, "The mechanism of the spontaneous autoxidation of dihydroartemisinic acid", Tetrahedron, vol. 58, pp. 897-908.

Teoh, K. H., Polichuk, D. R., Reed, D. W., Nowak, G., & Covello, P. S. 2006, "*Artemisia annua*L. (Asteraceae) trichome-specific cDNAs reveal CYP71AV1, a cytochrome P450 with a key role in the biosynthesis of the antimalarial sesquiterpene lactone artemisinin", FEBS Lett., vol. 580, No. 5, pp. 1411-1416.

Torrell, M., Garcia-Jacas, N., Susanna, A., & Valles, J. 1999, "Phylogeny in *Artemisia*(Asteraceae, Anthemideae) inferred from nuclear ribosomeal DNA (ITS) sequences", Taxon, vol. 48, p. 721.

van Agtmael, M. A., Eggelte, T. A., & van Boxtel, C. J. 1999b, "Artemisinin drugs in the treatment of malaria: from medicinal herb to registered medication", Trends Pharmacol.Sci., vol. 20, No. 5, pp. 199-205.

van de Loo, F. J., Turner, S., & Somerville, C. 1995, "Expressed sequence tags from developing castor seeds", Plant Physiology, vol. 108, pp. 1141-1150.

Wallaart, T. E., Bouwmeester, H. J., Hille, J., Poppinga, L., & Maijers, N. C. 2001, "Amorpha-4,11-diene synthase: cloning and functional expression of a key enzyme in the biosynthetic pathway of the novel antimalarial drug artemisinin", Planta, vol. 212, No. 3, pp. 460-465.

Wallaart, T.E., Van Uden, W., Luberink, H.G.M., Woerdenbag, H.J., Pras, N., & Quax, W.J. 1999, "Isolation and identification of dihydroartemisinic acid from *Artemisia annua*and its possible role in the biosynthesisi of artemisinin.", J Nat Prod, vol. 62, pp. 430-433.

Watson, L. E., Evans, T. M., & Boluarte, T. 2000, "Molecular phylogeny and biogeography of tribe Anthemideae (Asteraceae), based on chloroplast ndhF", Mol.Phylogen.Evol., vol. 15, pp. 59-69.

Wilairatana, P., Krudsood, S., Treeprasertsuk, S., Chalermrut, K., & Looareesuwan, S. 2002, "The future outlook of antimalarial drugs and recent work on the treatment of malaria", Arch.Med.Res., vol. 33, No. 4, pp. 416-421.

Jin, Z.; Zhao, D.; Qiao, C. and Fu, C. 2004, "Cloning and characterization of the aldehyde dehydrogenase gene from *Saussurea medusa*", Key Laboratory of Photosynthesis and Environmental Molecular Physiology, Institute of Botany, Chinese Academy of Sciences, GenBank AAT44126.

International Preliminary Report and Written Opinion, from corresponding application PCT/CA2007/000614, completed May 31, 2007.

Extended European Search Report on corresponding European application 07719541.0 dated Aug. 28, 2009.

EMBL Database accession No. EMBL:AB036735, Jan. 14, 2000.

Bouwmeester, et al. Medicinal and Aromatic Plants. p. 275-290, Apr. 17, 2005.

Bertea et al. Planta Medica. 71(1):40-47, Jan. 2005.

Bertea et al. Archives of Biochemistry and Biophysics. 448(1-2):3-12, Mar. 15, 2006.

GENPEPT Database accession No. AAT44126, Jun 13, 2004.

Ro et al. Nature. 220: 940-943, Apr 13, 2006.

Bertea et al., Identification of Intermediates and Enzymes Involved in the Early Steps of Artemisinin Biosynthesis in *Artemisia annua*, Planta Med 2005: 71:40-47.

Bouwmeester et al., Research to Improve Artemisinin Production for Use in the Preparation of Anti-Malarail Drugs, Medicinal and Aromatic Plants, 275-290, 2006.

Jin et al., Cloning and characterization of the aldehyde dehydrogenase gene from *Saussurea medusa*, EMBL Accession: AY550122, p. 1-2, European Bioinformatics Institute 2010.

Teoh et al., Molecular cloning of an aldehyde dehydrogenase implicated in artemisinin biosynthesis . . . , EMBL Accession: FJ809784, p. 1-2, European Bioinformatics Institute 2010.

Ro et al., Production of the antimalarial drug precursor artemisinic acid in engineered yeast, vol. 440, Apr. 13, 2006, p. 940-943, Nature Publishing Group.

Teoh et al., *Artemisia annua*L. (Asteraceae) trichome-specific cDNAs reveal CYP7IAVI, a cytochrome P450 with a key role . . . , FEBS Letters 580 (2006) 1411-1416.

Teoh et al., Molecular cloning of an aldehyde dehydrogenase implicated in artemisinin biosynthesis in *Artemisia annua*1, Botany 87: 635-642 (2009).

Extended European Search Report on European Application 09176132.0 published Aug. 5, 2010.

* cited by examiner

GACTTTTTAAATCCACCTCTTCAACCTTCAAAACTCAAAGAACATTTTCAACATGGAACAGCAACAAG
AAGTGATCACCAACAAGAAAGTAATACTAAAAGACTACGTTGTAGGGTTTCCTAAGGAGTCCGACATG
ATCCTTAAAACATCTGAAACCATGACACTGAAGCTTCCAGCAGGTTCTAATGGTTTACTTGTTAAGAA
TCTTTATTTGTCGTGTGATCCTTACATGCGTTCTCGCATGACTAAAACTGAAGGCAGTTATGTCGAGT
CTTTTACTCCTGGTTCGCCTCTAACAGGATATGGAGTAGCTAAGGTTCTTGAATCGGGCATGCAAAC
TTTAAGAAAGgCGACCTAATTTGGGGATTTACAGGATGGGAAGAGTACAGCATTATCAATGCTCCTGA
GGGTCTATTCAAGATTGAACATACCGATGTGCCTCTTTCTTATTATACAGGAATTCTTGGTATGCCTG
GCATGACTGCTTATGTTGGTTTCTATGAGATATGTACTCCAAAAAAAGGAGAGTATGTCTTTGTTTCG
GCTGCTTCTGGTGCAGTTGGGCAGCTGGTTGGGCAGTTTGCTAAGTTGTCCGGATGCTATGTTGTTGG
GAGTGCTGGTACGAAGGAAAAGGTTGATTTGCTGAAGAACAAATTTGGATTTGATGAAGCTTTTAATT
ACAAGGAAGAGCAAGATCTGGATGCGGCTCTGAAGAGGTACTTTCCCGAAGGAAtGATATTTACTTT
GAGAACGTTGGAGGAAGGATGTTGGATGCAGTACTCTTGAACATGAGACTAGATGGCCGAATTTCAGT
TTGTGGTATGATCTCACAATACAACTTAGAGCAaTCTGAGGGAGTGCGTAACCTCTTCACCCTCGTAA
CAAAACGTGTGACCATGAAAGGGTTCATTGTGTTTGATCACTATCACAAGTACCCAAAGTATCTAGAA
ATGATTATACCCCTAATTAAAAATGGCACGATAAATTACATAGAAGACATTGTAGAAGGGCTCGAGAA
TGCACCCGCGGCTTTGATTGGTCTGTATTCTGGAAAAAATGTTGGAAAGCAAGTGGTGGTGGTTGCGC
ATGAATGATGAAGAGTTAAGGCTAAATGGTGGTACTATGAATACTTTTTAGGTTTGATTTTGGTCAGA
GTGTGGGATTGTATGGAATAAATTTCTCCAAGTTCTAATACTTAGGGGGTGTTTGATTTCGACTTAAT
ATGAAAAAAATTAAATTAATTAAGTCATATGAAAACTGTTTGTTTGTGACTGAAAAAAAAAAAAAAAA
AAAA

SEQ ID No.: 1

FIG. 2

MEQQQEVITNKKVILKDYVVGFPKESDMILKTSETMTLKLPAGSNGLLVKNLYLSCD
PYMRSRMTKTEGSYVESFTPGSPLTGYGVAKVLESGHANFKKGDLIWGFTGWEEYSI
INAPEGLFKIEHTDVPLSYYTGILGMPGMTAYVGFYEICTPKKGEYVFVSAASGAVG
QLVGQFAKLSGCYVVGSAGTKEKVDLLKNKFGFDEAFNYKEEQDLDAALKRYFPEGI
DIYFENVGGRMLDAVLLNMRLDGRISVCGMISQYNLEQSEGVRNLFTLVTKRVTMKG
FIVFDHYHKYPKYLEMIIPLIKNGTINYIEDIVEGLENAPAALIGLYSGKNVGKQVV
VVAHE

SEQ ID No.: 2

FIG. 3

ATGTCGTACTACCATCACCATCACCATCACCTCGAATCAACAAGTTTGTACAAAAAAGCAGGCTCCGCG
GCCGCCCCCTTCACCATGGAACAGCAACAAGAAGTGATCACCAACAAGAAAGTAATACTAAAAGACTAC
GTTGTAGGGTTTCCTAAGGAGTCCGACATGATCCTTAAAACATCTGAAACCATGACACTGAAGCTTCCA
GCAGGTTCTAATGGTTTACTTGTTAAGAATCTTTATTTGTCGTGTGATCCTTACATGCGTTCTCGCATG
ACTAAAACTGAAGGCAGTTATGTCGAGTCTTTTACTCCTGGTTCGCCTCTAACAGGATATGGAGTAGCT
AAGGTTCTTGAATCTGGGCATGCAAACTTTAAGAAAGGCGACCTAATTTGGGGATTTACAGGATGGGAA
GAGTACAGCATTATCAATGCTCCTGAGGGTCTATTCAAGATTGAACATACCGATGTGCCTCTTTCTTAT
TATACAGGAATTCTTGGTATGCCTGGCATGACTGCTTATGTTGGTTTCTATGAGATATGTACTCCAAAA
AAAGGAGAGTATGTCTTTGTTTCGGCTGCTTCTGGTGCAGTTGGGCAGCTGGTTGGGCAGTTTGCTAAG
TTGTCCGGATGCTATGTTGTTGGGAGTGCTGGTACGAAGGAAAAGGTTGATTTGCTGAAGAACAAATTT
GGATTTGATGAAGCTTTTAATTACAAGGAAGAGCAAGATCTGGATGCGGCTCTGAAGAGGTACTTTCCC
GAAGGAATTGATATTTACTTTGAGAACGTTGGAGGAAGGATGTTGGATGCAGTACTCTTGAACATGAGA
CTAGATGGCCGAATTTCAGTTTGTGGTATGATCTCACAATACAACTTAGAGCAATCTGAGGGAGTGCGT
AACCTCTTCACCCTCGTAACAAAACGTGTGACCATGAAAGGGTTCATTGTGTTTGATCACTATCACAAG
TACCCAAAGTATCTAGAAATGATTATACCCCTAATTAAAAATGGCACGATAAATTACATAGAAGACATT
GTAGAAGGGCTCGAGAATGCACCCGCGGCTTTGATTGGTCTGTATTCTGGAAAAAATGTTGGAAAGCAA
GTGGTGGTGGTTGCGCATGAATGA

SEQ ID No.: 3

FIG. 4

MSYYHHHHHHLESTSLYKKAGSAAAPFTMEQQQEVITNKKVILKDYVVGFPKESDMILKTSETMTLKLP
AGSNGLLVKNLYLSCDPYMRSRMTKTEGSYVESFTPGSPLTGYGVAKVLESGHANFKKGDLIWGFTGWE
EYSIINAPEGLFKIEHTDVPLSYYTGILGMPGMTAYVGFYEICTPKKGEYVFVSAASGAVGQLVGQFAK
LSGCYVVGSAGTKEKVDLLKNKFGFDEAFNYKEEQDLDAALKRYFPEGIDIYFENVGGRMLDAVLLNMR
LDGRISVCGMISQYNLEQSEGVRNLFTLVTKRVTMKGFIVFDHYHKYPKYLEMIIPLIKNGTINYIEDI
VEGLENAPAALIGLYSGKNVGKQVVVVAHE

SEQ ID No.: 4

FIG. 5

```
TGACTCACTATAGGGGCGCTAGCTCGCCGCAGCCGAACGACCGAGCGCAGCGAGTCAGTGAGCGAGGAA
GCGGCCGCATAACTTCGTATAGCATACATTAGATTCGACCCTTGAATAAAAATTTCATAAAAAACAAAG
ATGAGCTCAGGAGCTAATGGAAGTTCTAAGTCAGCAAGCCATAAAATCAAGTTCACCAAGCTTTTTATC
AATGGCGAATTTGTTGATTCTATTTCAGGAAACACTTTTGACACGATTAATCCAGCGACAGAAGAAGTG
TTAGCAACAGTGGCCGAAGGAAGAAAGGAAGACATTGATTTGGCCGTTAAGGCTGCCCGTGAAGCTTTC
GACAATGGACCTTGGCCTCGCATGTCTGGCGAGGCACGCCGAAAAATCATGTTAAAGTTCGCAGACTTG
ATCGATGAAAATGCTGACGAGTTAACCACCTTAGAAGTAATCGATGGAGGAAAATTGTTTGGCCCAGTG
AGGCACTTTGAAGTCCCGGTTTCATCAGATACATTTCGTTACTTTGCGGGTGCAGCCGATAAAATCCGT
GGAGCAACTCTTAAAATGTCAAGTAATATTCAAGCTTATACGCTACGTGAACCCATCGGAGTAGTTGGT
CACATCATTCCTTGGAATGGTCCTGCCTTCATGTTCGCTACAAAGGTTGCACCAGCTTTAGCTGCTGGC
TGCACCATGGTCATCAAGCCTGCCGAACATACTCCCCTTACAGTTCTCTTTTAGCTCACCTGTCGAAG
CTGGCTGGTGTTCCTGATGGCGTGATTAATGTGGTTAACGGGTTTGGAAAAACTGCTGGTGCTGCCGTT
AGCTCGCATATGGACATTGACATGGTTACTTTTACGGGATCCACAGAAGTTGGCCGCACCGTAATGCAA
GCTGCAGCTCTAAGTAATCTGAAACCAGTGTCACTCGAACTTGGAGGAAAATCGCCTTTGATTGTTTTC
GATGATGCAGATGTTGATAAAGCCGCAGAATTTGCTATTTTGGGAAATTTTACTAACAAAGGTGAGATG
TGTGTGGCAGGGTCTCGTGTTTTCGTTCAGGAAGGGATCCATGACGTATTCGTAAAAAAATTGGAAGGA
GCGGTGAAAGCGTGGGCAACAAGGGACCCTTTTGATCTCGCCACTCGTCATGGACCTCAGAATAACAAA
CAACAATATGATAAAGTACTTTCATGCATCAACCATGGCAAAAAGGAAGGTGCGACTTTGGTAACCGGT
GGTAAGCCATTTGGGAAGAAAGGATACTACATTGAGCCTACTCTATTTACAAACGTTACGGATGATATG
ACCATAGCAAAGGAAGAAATTTTTGGCCCCGTTATATCTGTTCTCAAGTTCAAGACTGTTGAAGAAGTG
ATTAAAAGAGCAAATGCCACAAAATATGGACTTGCCTCAGGTGTATTCACCAAAAATATTGATGTCGTG
AACACAGTTTCGAGATCTATTCGAGCAGGTGCTGTTTGGGTCAACTGTTATTTAGCACTCGACCGGGAT
GCACCTCATGGAGGGTATAAAATGAGTGGGTTTGGACGAGAACAAGGATTAGAGGCACTTGAACATTAT
CTTCAGATTAAGACAGTGGCTACACCCATATATGATTCCCCGTGGCTCTAAACTTTCATATTTGTTTGT
TTATCAAATAAGAAGACTGCGGTCCATTTATCGAATATTTCGTTTGATGTATGAGTTTTAATGAATAAA
GCGCAACTACTTGTGCATACTTGTTGCTAATGAAATGTATCAAAAAAAAAAAAAAAAAAA
```

SEQ ID NO.: 5

Fig. 6

```
MSSGANGSSKSASHKIKFTKLFINGEFVDSISGNTFDTINPATEEVLATVAEGRKEDIDLAVKAAREAF
DNGPWPRMSGEARRKIMLKFADLIDENADELTTLEVIDGGKLFGPVRHFEVPVSSDTFRYFAGAADKIR
GATLKMSSNIQAYTLREPIGVVGHIIPWNGPAFMFATKVAPALAAGCTMVIKPAEHTPLTVLFLAHLSK
LAGVPDGVINVVNGFGKTAGAAVSSHMDIDMVTFTGSTEVGRTVMQAAALSNLKPVSLELGGKSPLIVF
DDADVDKAAEFAILGNFTNKGEMCVAGSRVFVQEGIHDVFVKKLEGAVKAWATRDPFDLATRHGPQNNK
QQYDKVLSCINHGKKEGATLVTGGKPFGKKGYYIEPTLFTNVTDDMTIAKEEIFGPVISVLKFKTVEEV
IKRANATKYGLASGVFTKNIDVVNTVSRSIRAGAVWVNCYLALDRDAPHGGYKMSGFGREQGLEALEHY
LQIKTVATPIYDSPWL
```

SEQ ID NO.: 6

Fig. 7

```
ATGTCGTACTACCATCACCATCACCATCACCTCGAATCAACAAGTTTGTACAAAAAAGCAGGCTCCGCG
GCCGCCCCCTTCACCATGAGCTCAGGAGCTAATGGAAGTTCTAAGTCAGCAAGCCATAAAATCAAGTTC
ACCAAGCTTTTTATCAATGGCGAATTTGTTGATTCTATTTCAGGAAACACTTTTGACACGATTAATCCA
GCGACAGAAGAAGTGTTAGCAACAGTGGCCGAAGGAAGAAAGGAAGACATTGATTTGGCCGTTAAGGCT
GCCCGTGAAGCTTTCGACAATGGACCTTGGCCTCGCATGTCTGGCGAGGCACGCCGAAAAATCATGTTA
AAGTTCGCAGACTTGATCGATGAAAATGCTGACGAGTTAACCACCTTAGAAGTAATCGATGGAGGAAAA
TTGTTTGGCCCAGTGAGGCACTTTGAAGTCCCGGTTTCATCAGATACATTTCGTTACTTTGCGGGTGCA
GCCGATAAAATCCGTGGAGCAACTCTTAAAATGTCAAGTAATATTCAAGCTTATACGCTACGTGAACCC
ATCGGAGTAGTTGGTCACATCATTCCTTGGAATGGTCCTGCCTTCATGTTCGCTACAAAGGTTGCACCA
GCCTTAGCTGCTGGCTGCACCATGGTCATCAAGCCTGCCGAACATACTCCCCTTACAGTTCTCTTTTTA
GCTCACCTGTCAAGCTGGCTGGTGTTCCTGATGGCGTGATTAATGTGGTTAACGGGTTTGGAAAAACT
GCTGGTGCTGCCGTTAGCTCGCATATGGACATTGACATGGTTACTTTTACGGGATCCACAGAAGTTGGC
CGCACCGTAATGCAAGCTGCAGCTCTAAGTAATCTGAAACCAGTGTCACTCGAACTTGGAGGAAAATCG
CCTTTGATTGTTTCGATGATGCAGATGTTGATAAAGCCGCAGAATTTGCTATTTTGGGAAATTTTACT
AACAAAGGTGAGATGTGTGTGGCAGGGTCTCGTGTTTTCGTTCAGGAAGGGATCCATGACGTATTCGTA
AAAAAATTGGAAGGAGCGGTGAAAGCGTGGGCAACAAGGGACCCTTTTGATCTCGCCACTCGTCATGGA
CCTCAGAATAACAAACAACAATATGATAAAGTACTTTCATGCATCAACCATGGCAAAAAGGAAGGTGCG
ACTTTGGTAACCGGTGGTAAGCCATTTGGGAAGAAAGGATACTACATTGAGCCTACTCTATTTACAAAC
GTTACGGATGATATGACCATAGCAAAGGAAGAAATTTTTGGCCCCGTTATATCTGTTCTCAAGTTCAAG
ACTGTTGAAGAAGTGATTAAAAGAGCAAATGCCACAAAATATGGACTTGCCTCAGGTGTATTCACCAAA
AATATTGATGTCGTGAACACAGTTTCGAGATCTATTCGAGCAGGTGCTGTTTGGGTCAACTGTTATTTA
GCACTCGACCGGGATGCACCTCATGGAGGGTATAAAATGAGTGGGTTTGGACGAGAACAAGGATTAGAG
GCACTTGAACATTATCTTCAGATTAAGACAGTGGCTACACCCATATATGATTCCCCGTGGCTTTAA
```

SEQ ID NO.: 7

FIG. 8

```
MSYYHHHHHHLESTSLYKKAGSAAAPFTMSSGANGSSKSASHKIKFTKLFINGEFVDSISGNTFDTINP
ATEEVLATVAEGRKEDIDLAVKAAREAFDNGPWPRMSGEARRKIMLKFADLIDENADELTTLEVIDGGK
LFGPVRHFEVPVSSDTFRYFAGAADKIRGATLKMSSNIQAYTLREPIGVVGHIIPWNGPAFMFATKVAP
ALAAGCTMVIKPAEHTPLTVLFLAHLSKLAGVPDGVINVVNGFGKTAGAAVSSHMDIDMVTFTGSTEVG
RTVMQAAALSNLKPVSLELGGKSPLIVFDDADVDKAAEFAILGNFTNKGEMCVAGSRVFVQEGIHDVFV
KKLEGAVKAWATRDPFDLATRHGPQNNKQQYDKVLSCINHGKKEGATLVTGGKPFGKKGYYIEPTLFTN
VTDDMTIAKEEIFGPVISVLKFKTVEEVIKRANATKYGLASGVFTKNIDVVNTVSRSIRAGAVWVNCYL
ALDRDAPHGGYKMSGFGREQGLEALEHYLQIKTVATPIYDSPWL
```

SEQ ID NO.: 8

FIG. 9.

NUCLEOTIDE SEQUENCES ENCODING ENZYMES IN BIOSYNTHESIS OF DIHYDROARTEMISINIC ACID

CROSS-REFERENCE TO RELATED APPLICATIONS

This application is a national entry of PCT/CA2007/000614 filed Apr. 4, 2007 and claims the benefit of U.S. Provisional Patent Application Ser. No. 60/789,138 filed Apr. 5, 2006 and U.S. Ser. No. 60/857,503 filed Nov. 8, 2006, both of which are herein incorporated by reference in their entirety.

FIELD OF THE INVENTION

The present invention relates to production of plant-derived compounds of health and commercial interest. More particularly, the present invention relates to nucleotide sequences encoding enzymes, to enzymes encoded by the nucleotide sequences and to processes for producing (11S)-dihydroartemisinic aldehyde, (11R)-dihydroartemisinic acid and/or artemisinic acid therewith.

BACKGROUND OF THE INVENTION

Plants, in general, contain a myriad of secondary metabolites often synthesized by unique biochemical processes operating only in exotic species. For plant-derived products such as drugs, the 1997 worldwide sales were US$ 10 billion (Rotheim 2002). In many cases the supply of the relevant plant material for these drugs is limited or variable. One approach to developing methods for producing these drugs is to apply the methods of biochemistry, molecular biology and genomics to elucidate the biosynthesis and relevant biosynthetic genes for compounds of value for human health.

With the realization that many of the enzymes involved in natural product biosynthesis represent variations within known classes of enzymes, expressed sequence tag (EST) analysis (combined with heterologous expression) provides a powerful means of identifying their corresponding genes (Cahoon et al. 1999, Gang et al. 2001, Lange et al. 2000 and van de Loo et al. 1995)

One area of interest is bioactive compounds of the tribe Anthemideae in the family Asteraceae (Compositae) (Torrell et al. 1999 and Watson et al. 2000). Anthemideae (Asteraceae, subfamily Asteroideae) is a tribe of 109 genera which includes daisies, chrysanthemums, tarragon, chamomile, yarrow and sagebrushes (Watson et al. 2000). These plants are aromatic in nature resulting from high concentrations of mono- and sesqui-terpenes. Many of the species in this tribe are valued for the health benefits or insecticidal properties.

Of particular interest is artemisinin from *Artemisia annua* or sweet wormwood. In 1972, Chinese scientists isolated the sesquiterpene lactone containing an endoperoxide group (see FIG. 1) from *Artemisia* and called it qinghaosu (van Agtmael et al. 1999b). Prior to this sweet wormwood or qinghao had been used in traditional Chinese medicine for centuries. Artemisinin has become very important for the treatment of malaria in Southeast Asia and elsewhere, particularly for multi-drug-resistant falciparum forms of the disease (O'Neill 2005, Rathore et al. 2005, Robert et al. 2002, Wilairatana et al. 2002 and Wu 2002). Since the discovery of artemisinin, a number of semi-synthetic derivatives have been developed for specific applications in malaria treatment.

Malaria remains a serious health problem which affects over 400 million people, especially in Africa and Southeast Asia, causing the deaths in excess of 2 million each year. Increasing resistance of the malaria parasite, *Plasmodium falciparum*, towards current antimalarial drugs is a cause for concern. The future value of antimalarial drugs based on the artemisinin structure is illustrated by the development by Bayer AG of Artemisone, an artemisinin derivative reported to be 10-30 fold more active than artesunate, for which clinical trials are currently under way. Also, researchers at the Walter Reed Army Institute of Research (USA) are currently developing artelinic acid for intravenous treatment of severe malaria.

Artemisinin is produced in relatively small amounts of 0.01 to 1.0% dry weight, making it and its derivatives relatively expensive (Gupta et al. 2002). Several studies describe the chemical synthesis of the sesquiterpene, but none are an economical alternative for isolation of artemisinin from the plant (Yadav et al. 2003). Therefore a higher concentration in the plant or production in an alternative host is desirable to make artemisinin available as economically as possible, especially for use in the Third World. Knowledge of the biosynthetic pathway and the genes involved should enable engineering of improved production of artemisinin. Alternatively, there is also the possibility of producing intermediates in the pathway to artemisinin which are of commercial value. For example, a compound 15 times more potent in vitro than artemisinin against *Plasmodium falciparum* has been synthesized from artemisinic alcohol (Jung et al. 2001).

There is evidence that artemisinin is localized to glandular trichomes on the surfaces of certain tissues of the plant (Duke et al. 1994 and Duke et al. 1993). The number and even existence of these trichomes and the amount of artemisinin varies widely among biotypes.

Typically, compounds discovered in plants and found to be useful are produced commercially by i) chemical synthesis, where possible and economical, ii) extraction of cultivated or wild plants, or iii) cell or tissue culture (this is rarely economical). In those cases in which chemical synthesis is not economical, it makes sense to learn as much as possible about the biosynthesis of a natural product, such that it can be produced most efficiently in plants or cell/tissue culture. In the case of artemisinin, chemical synthesis is not commercially feasible. Since the compound is produced in small quantities in *Artemisia*, the drugs derived from artemisinin are relatively expensive, particularly for the Third World countries in which they are used. While the antimalarial drugs, chloroquine and sulfadoxine-pyrimethamine, cost as little as 20 cents for an adult treatment, artemisinin-derived compounds, by contrast, can be 100 times as expensive. Chloroquine resistance is prevalent and sulfadoxine-pyrimethamine resistance is increasing. The World Health Organization recently added the artemisinin-derived drug, artemether to their Model List of Essential Medicines, which are recommended to be available at all times in adequate amounts and in the appropriate dosage forms, and at a price that individuals and the community can afford. Consequently, it would be useful to be able to supply artemisinin-derived drugs more economically.

There are numerous patents relating to artemisinin and artemisinin derived drugs. These cover drug synthesis and formulation, *Artemisia* cultivation (Kumar 2002) and tissue culture and artemisinin extraction (Elferaly 1990). Commonly owned U.S. patent application 60/729,210 filed Oct. 24, 2005, the disclosure of which is herein incorporated by reference, and now filed as a PCT patent application, discloses a gene encoding amorpha-4,11-diene hydroxylase, which catalyzes the first committed steps in artemisinin biosynthesis (FIG. 1).

In the past five years a reasonably clear picture of artemisinin biosynthesis has emerged as illustrated in FIG. 1 (Bertea et al. 2005). The identity of amorpha-4,11-diene as a biosynthetic intermediate was established, based on the presence of trace of amorpha-4,11-diene in *Artemisia* extracts and the cloning and expression of cDNAs representing amorpha-4,11-diene synthase, a terpene cyclase (Bouwmeester et al. 1999 and Wallaart et al. 2001). A cytochrome P450 gene designated cyp71av1 was recently cloned and characterized (Teoh et al. 2006). The cyp71av1 gene encodes a hydroxylase that catalyzes the conversion of amorpha-4,11-diene to artemisinic alcohol. CYP71AV1 expressed in yeast is also capable of oxidizing artemisinic alcohol to artemisinic aldehyde and artemisinic aldehyde to artemisinic acid.

SUMMARY OF THE INVENTION

The invention described herein addresses the production of artemisinin and artemisinin-related compounds, including precursors, of pharmaceutical and commercial interest.

There is provided an isolated nucleic acid molecule comprising a nucleotide sequence having at least 70% nucleotide sequence identity to SEQ ID No.: 3 and encoding an artemisinic aldehyde double bond reductase.

There is provided an isolated nucleic acid molecule comprising a nucleotide sequence having at least 70% nucleotide sequence identity to SEQ ID No.: 7 and encoding an artemisinic/dihydroartemisinic aldehyde dehydrogenase.

There is provided an isolated nucleic acid molecule comprising a nucleotide sequence encoding an artemisinic aldehyde double bond reductase having an amino acid sequence with at least 70% amino acid sequence identity to SEQ ID No.: 2.

There is provided an isolated nucleic acid molecule comprising a nucleotide sequence encoding an artemisinic/dihydroartemisinic aldehyde dehydrogenase having an amino acid sequence with at least 70% amino acid sequence identity to SEQ ID No.: 6.

There is provided a purified artemisinic aldehyde double bond reductase having an amino acid sequence with at least 70% amino acid sequence identity to SEQ ID No.: 2.

There is provided a purified artemisinic aldehyde double bond reductase having an amino acid sequence with at least 70% amino acid sequence identity to SEQ ID No.: 6.

There is provided a use of one or more isolated nucleic acid molecules of the present invention in the production of (11S)-dihydroartemisinic aldehyde, (11R)-dihydroartemisinic acid and/or artemisinic acid.

There is provided a use of one or more of a purified artemisinic aldehyde double bond reductase or artemisinic/dihydroartemisinic aldehyde dehydrogenase encoded by one or more isolated nucleic acid molecules of the present invention in the production of (11S)-dihydroartemisinic aldehyde, (11R)-dihydroartemisinic acid and/or artemisinic acid.

There is provided a process for producing (11S)-dihydroartemisinic aldehyde, (11R)-dihydroartemisinic acid and/or artemisinic acid comprising expressing or overexpressing one or more isolated nucleic acid molecules of the present invention in a host cell.

There is provided a process for producing (11S)-dihydroartemisinic aldehyde, (11R)-dihydroartemisinic acid and/or artemisinic acid comprising producing or overproducing an artemisinic aldehyde double bond reductase and/or artemisinic/dihydroartemisinic aldehyde dehydrogenase of the present invention in a host cell.

The isolated nucleic acid molecules are preferably derived from *A. annua*.

Overexpression of one or more of the nucleic acid molecules or overproduction of the artemisinic aldehyde double bond reductase and/or artemisinic/dihydroartemisinic aldehyde dehydrogenase may be done in *A. annua*. Expression of one or more of the nucleic acid molecules or expression of the artemisinic aldehyde double bond reductase and/or artemisinic/dihydroartemisinic aldehyde dehydrogenase may be done in other hosts, for example plants, yeasts or bacteria. Overexpression or expression of one or more of the isolated nucleic acid molecules of the present invention may be done in combination with overexpression or expression of one or more other nucleic acid molecules involved in the biosynthesis of artemisinin, for example amorpha-4,11-diene synthase and/or amorpha-4,11-diene hydroxylase.

Part of the solution to the problem of producing artemisinin in an economical and timely fashion is the isolation and exploitation of genes involved in artemisinin biosynthesis. As in other examples of metabolic engineering, such genes can be used to enhance production by overexpression in the native plant (*A. annua*), a different plant, or in micro-organisms such as bacteria or yeast. An example of this is the expression of the amorphadiene synthase gene in *E. coli* to produce the artemisinin precursor amorphadiene (Martin et al. 2003) and the production of artemisinic acid in yeast (Ro et al. 2006). Two important steps in the pathway to artemsinin per se, are the reduction of artemisinic aldehyde to (11R)-dihydroartemisinic aldehyde and the oxidation of (11R-dihydroartemisinic aldehyde to (11R)-dihydroartemisinic acid. Consequently, the genes involved in these steps may be used to produce (11R)-dihydroartemisinic acid in a host, alone or in combination with each other and/or with one or more of amorphadiene synthase and amorphadiene hydroxylase.

The resulting (11R)-dihydroartemisinic acid could then be chemically converted to artemisinin or related compounds of commercial value. Dihydroartemisinic acid is the presumed immediate precursor of artemisinin, and its transformation to artemisinin has been shown to occur spontaneously through photo-oxidation, requiring no enzyme intervention (Sy et al. 2002 and Wallaart et al. 1999). Consequently, using (11R)-dihydroartemisinic acid instead of artemisinic acid as the starting material for semi-synthesis of artemisinin reduces the number of steps required for artemisinin production thus, simplifying the production process. This may lead to shorter artemisinin production time and lower production cost. The eventual outcome will be cheaper artemisinin and artemisinin-related drugs. Alternatively, (11S)-dihydroartemsinic acid could be chemically converted to (11S)-artemisinin which is expected to have antimalarial activity.

The genes (nucleic acid molecules) of the present invention may be derived, for example cloned, from *Artemisia annua*. Cloned nucleic acid molecules were sequenced and characterized by expression in *E. coli*. One of the cloned nucleic acid molecules encodes a double-bond reductase which reduces the C11-C13 double bond of artemisinic aldehyde to form (11S)-dihydroartemisinic aldehyde as the major product. Another of the cloned nucleic acid molecules encodes an aldehyde dehydrogenase for the conversion of dihydroartemisinic aldehyde to dihydroartemisinic acid. The aldehyde dehydrogenase is further capable of dehydrogenating artemisinic aldehyde to artemisinic acid.

Nucleic acid molecules of the present invention may also be used in the development of DNA markers and in targeted mutagenesis techniques (e.g. TILLING (Targeting Induced Local Lesions IN Genomes)).

A genetic marker (DNA marker) is a segment of DNA with an identifiable physical location on a chromosome and associated with a particular gene or trait and whose inheritance can be followed. A marker can be a gene, or it can be some section of DNA with no known function. Because DNA segments that lie near each other on a chromosome tend to be inherited together, markers are often used as indirect ways of tracking the inheritance pattern of a gene that has not yet been identified, but whose approximate location is known. Thus, markers can assist breeders in developing populations of organism having a particular trait of interest. Gene-specific markers can be used to detect genetic variation among individuals which is more likely to affect phenotypes relating to the function of a specific gene. For example, variation in a gene-specific marker based on AaALDH1, rather than variation in an anonymous DNA marker, would be more likely linked to variation in content of artemisinin or related compounds, by virtue of its association with the relevant biosynthetic pathway. In one embodiment, a DNA marker for AaALDH1 could be developed by sequencing the polymerase chain reaction amplified AaALDH1 gene from a number of individual plants of Artemisia annua. Such sequencing would provide information about sequence polymorphisms within the gene. A range of methods available to those skilled in the art could be used to detect such polymorphisms, including cleaved amplified polymorphic sequences (CAPs) (Konieczy et al. 1993).

The presence of such gene-specific polymorphisms could be correlated with levels of artemisinin or related compounds and used in a breeding program to select and/or develop lines of Artemisia annua with enhanced levels of artemisinin or related compounds. That is, the variation in genetic structure may be detected in other plants, and the plants with the variation selectively bred to produce a population of plants having increased levels of dihydroartemisinic aldehyde, dihydroartemisinic acid, artemisinic acid and/or artemisinin compared to a population of control plants produced under similar conditions. Genetic markers are discussed in more detail in Bagge et al. 2007, Pfaff et al. 2003, Sandal et al. 2002 and Stone et al. 2002.

TILLING (Bagge et al. 2007, Comai et al. 2006, Henikoff, et al. 2004 and Slade et al. 2005) involves treating seeds or individual cells with a mutagen to cause point mutations that are then discovered in genes of interest using a sensitive method for single-nucleotide mutation detection. Detection of desired mutations (e.g. mutations resulting in a change in expression of the gene product of interest) may be accomplished, for example, by PCR methods. For example, oligonucleotide primers derived from the gene (nucleic acid molecule) of interest, such as the nucleic acid molecules of the present invention, may be prepared and PCR may be used to amplify regions of the gene of interest from plants in the mutagenized population. Amplified mutant genes may be annealed to wild-type genes to find mismatches between the mutant genes and wild-type genes. Detected differences may be traced back to the plants which had the mutant gene thereby revealing which mutagenized plants will have the desired expression. These plants may then be selectively bred to produce a population having the desired expression.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 2 depicts the nucleotide sequence (SEQ ID No.: 1) of the cDNA insert of pKT104 encoding Artemisia annua AaDBR1.

FIG. 3 depicts the predicted amino acid sequence (SEQ ID No.: 2) of the protein encoded by Artemisia annua gene AaDBR1.

FIG. 4 depicts the nucleotide sequence (SEQ ID No.: 3) of the open reading frame of the DNA insert in pKT032.

FIG. 5 depicts the predicted amino acid sequence (SEQ ID No.: 4) of the product of the AaDBR1 insert in pKT032 in frame with an N-terminal His tag sequence.

FIG. 6 depicts the nucleotide sequence (SEQ ID No.: 5) of the cDNA insert of pKT150 encoding Artemisia annua AaALDH1.

FIG. 7 depicts the predicted amino acid sequence (SEQ ID No.: 6) of the protein encoded by the Artemisia annua gene AaALDH1.

FIG. 8 depicts the nucleotide sequence (SEQ ID No.: 7) of the open reading frame of the DNA insert in pKT041.

FIG. 9 depicts the predicted amino acid sequence (SEQ ID No.: 8) of the product of the AaALDH1 insert in pKT041 in frame with an N-terminal His tag sequence.

DESCRIPTION OF PREFERRED EMBODIMENTS

Figure 1:
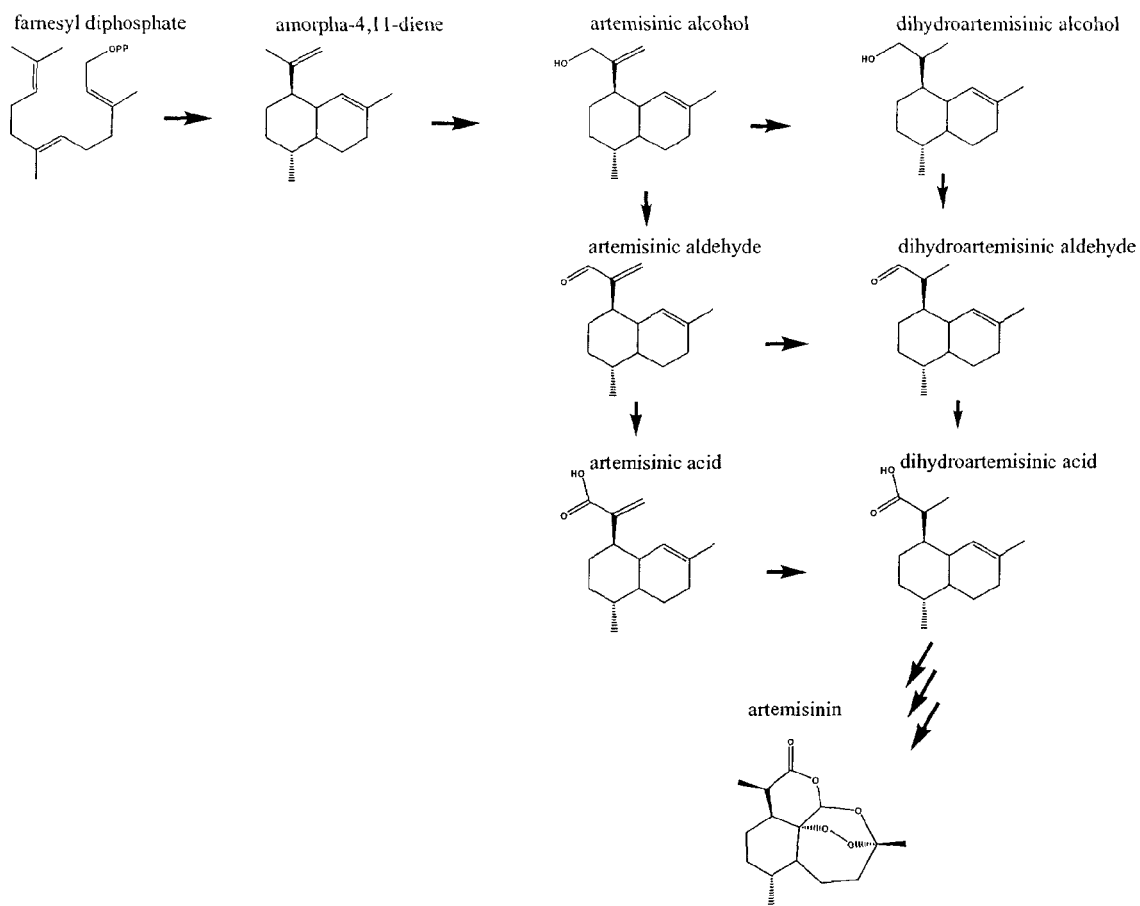
FIG. 1 depicts the proposed biosynthetic pathway for artemisinin biosynthesis.

Materials and Methods:
Artemisinic Aldehyde

Artemisinic acid was isolated from dichloromethane extracts of A. annua flower buds and leaves and was used to synthesize artemisinic aldehyde according to the method described by Chang et al. 2000, the disclosure of which is incorporated herein by reference.

Dihydroartemisinic Acid

Dihydroartemisinic acid was isolated and purified from A. annua leaf material obtained from a "line 2/39" containing relatively high levels of the dihydroartemisinic acid using the method described for artemisinic acid in Teoh et al. 2006, the disclosure of which is incorporated herein by reference.

Dihydroartemisinic Aldehyde

Dihydroartemisinic aldehyde was synthesized from the isolated dihydroartemisinic acid. The acid was converted to methyl dihydroartemisinate with excess diazomethane in diethyl ether at 0° C. for 5 minutes. The ether and diazomethane were removed under a stream of nitrogen and the methyl ester was reduced to (11R)-dihydroartemisinic alcohol with excess 1.5 M diisobutyl aluminum hydride in toluene at room temperature for 10 min under nitrogen. With subsequent extraction, oxidation to the aldehyde with pyridinium chlorochromate (Corey & Suggs 1975) and purification by HPLC the (11R)-dihydroartemisinic aldehyde was produced at an overall yield of 48% with >99% purity according to GC analysis.

Plant Materials

*Artemisia annua* L. seeds were obtained from Elixir Farm Botanicals, Brixey, Mo., USA and from Pedro Melillo de Magalhães, State University of Campinas, Brazil (line 2/39). Seeds were germinated and grown in soil in a controlled environment chamber with 16 hour/25° C. days and 8 hour/20° C. nights. Plants that had reached the height of approximately 1.2 m (about 3 months) were transferred to flowering chamber with 12 hour/25° C. days and 12 hour/20° C. nights. Flower buds that developed after 19-21 days in the flowering chamber were harvested for total RNA isolation.

cDNA Library Construction And Expressed Sequence Tag (EST) Analysis

Total RNA was extracted and isolated from glandular trichomes and flower buds using a modified method described by Logeman, et al. 1987. cDNA synthesis from 1.5 micrograms of total RNA and construction of the trichome and flower bud cDNA library were carried out with Creator™ SMART™ cDNA Library Construction Kit (Clontech). A total of 6,239 clones and 2,208 clones for trichome and flower bud libraries, respectively were randomly picked and their DNA sequences determined. Sequencing was performed on an AB13700 DNA sequencer using BigDye Terminator Cycle Sequencing Kit (Applied Biosystems) and the M13 reverse primer. DNA sequence traces were interpreted and vector and low quality sequences were eliminated using PHRED (Ewing et al. 1998) and LUCY (Chou & Holmes 2001). Clustering of the resulting EST dataset was done using STACKPACK (Miller et al. 1999) and sequence similarity was identified by BLAST (Altschul et al. 1990).

Isolation of Full-Length AaDBR1 cDNA

The open reading frame (ORF) of a double bond reductase designated AaDBR1, encoded by the EST clone pKT104, was obtained through PCR using gene-specific primers 5'-CACCATGGAACAGCAACMGAAG-3' (SEQ ID No.: 9) and 5'-TCATTCATGCGCAACCACCACCA-3' (SEQ ID No.: 10) and Vent polymerase (New England BioLabs, Cambridge, Mass., USA). The resulting PCR product was cloned via the Gateway entry vector pENTR/D/TOPO (Invitrogen) into a Gateway destination vector, pDEST17 (Invitrogen) to generate a bacteria expression clone pKT032. The ORF of AaDBR1 was cloned in frame with the 6×His-tag (SEQ ID No.: 13) at the N-terminal of AaDBR1.

Isolation of Full-Length AaALDH1 cDNA

The open reading frame (ORF) of an aldehyde dehydrogenase designated AaALDH1, encoded by the EST clone pKT150, was obtained through PCR using gene-specific primers 5'-CACCATGAGCTCAGGAGCTAAT-3' (SEQ ID No.:11) and 5'-TTAAAGCCACGGGGAATCATAT-3' (SEQ ID No. 12) and Vent polymerase (New England BioLabs, Cambridge, Mass., USA). The resulting PCR product was cloned via the Gateway entry vector pENTR/D/TOPO (Invitrogen) into a Gateway destination vector, pDEST17 (Invitrogen) to generate a bacterial expression clone pKT041. The ORF of AaALDH1 was cloned in frame with the 6×His-tag (SEQ ID No.: 13) at the N-terminal of AaALDH1.

Expression in *E. coli*

The plasmid pKT032 or pKT041 was introduced into *E. coli* strain BL21(DE3) (Novagen) using heat shock at 42° C. The GUS gene (Invitrogen) was cloned into pDEST17 to replace the ccdB gene and the construct pDEST-GUS introduced into the *E. coli* strain BL21(DE3) was used as a control. Transformants were grown on Luria Broth (LB) and selected on ampicillin (100 µg/mL) at 37° C. for 24 hours. A single colony containing pKT032 or pKT041 was used to inoculate 5 mL of LB liquid medium with ampicillin (LBA) and grown at 37° C. overnight with shaking. The overnight culture was used to inoculate 250 mL of LBA liquid medium and grown at 37° C. with shaking to an $OD_{600}$ of 0.6 per mL followed by induction with 1 mM IPTG and grown at 30° C. overnight with shaking. Cells were pelleted at 2,000 g at 4° C. for 10 minutes. The pelleted cells were resuspended in 6 mL of lysis buffer consisting of 50 mM sodium phosphate, pH 8.0, 0.1 M NaCl, 20 mM imidazole and 1 mM phenylmethylsufonyl fluoride (PMSF). Cells were lysed with lysozyme (0.2 mg/mL of cells) on ice for 30 minutes followed by sonication on ice with 30s pulse (5×). Protein concentration was determined by Bradford assay (Bio-Rad). The AaDBR1 protein was detected by silver stain on SDS gel and confirmed by Western Blot using Anti-His antibody (Invitrogen). The AaALDH1 protein was detected by Rapid Stain (Bioscience, St. Louis, Mo.) on SDS gel.

Purification of Recombinant AaALDH1

Cell-free extract of recombinant AaALDH1 was prepared as described above. The cell-free extract was centrifuged at 20,000 g at 4° C. for 15 minutes to remove any remaining insoluble materials before loading onto a His-Trap FF column (Amersham Bioscience, N.J.) equilibrated with binding buffer (20 mM sodium phosphate buffer containing 500 mM NaCl and 20 mM imidazole at pH 7.5). The column was washed with 5 column volume of binding buffer and the recombinant AaALDH1 eluted with elution buffer (20 mM sodium phosphate, 500 mM NaCl, pH 7.5) containing increasing concentration of imidazole in a step-wise fashion. The eluted fractions were concentrated and desalted in centrifugal filter devices (Amicon Ultra—15) (Millipore, Mass.) following manufacturer's protocol. The purity of the recombinant AaALDH1 was checked with SDS gel stained with Rapid Stain (Biosciences, St. Louis, Mo.).

In Vitro Cell-Free Assays

Cell-free extracts of recombinant His-tagged AaDBR1 protein were assayed with artemisinic aldehyde, followed by analysis by gas chromatography/mass spectrometry. Enzyme reactions were initiated by adding the substrate (5 µg) to 500 µL sodium phosphate buffer (50 mM, pH 7.5) containing 10% sorbitol, 1 mM NADPH, 2 mM DTT and 0.8 µg of enzyme. Negative controls were carried out with boiled proteins, without NADPH and with extracts from *E. coli* into which the construct pDEST17-GUS had been introduced. Reactions were allowed to proceed for 30 minutes at 30° C. with shaking and immediately stopped by extracting twice with 700 µL diethyl ether. The ether extracts were pooled, evaporated and taken up in 20 µL ethyl acetate (Sigma) followed by GC-MS analysis.

Cell-free extract of recombinant His-tagged AaALDH1 protein were assayed with dihydroartemisinic aldehyde and other substrates, followed by analysis by gas chromatography/mass spectrometry. Enzyme reactions were initiated by adding the substrate (5 µg) to 500 µL Tris-HCl buffer (50 mM, pH 8.5) containing, 1 mM NADP, and 1.0 µg of enzyme. Negative controls were carried out with boiled proteins, without NADP and with extracts from *E. coli* into which the construct pDEST17-GUS had been introduced. Reactions were allowed to proceed for 30 minutes at 30° C. with shaking and immediately stopped by extracting twice with 700 µL diethyl ether. The ether extracts were pooled, derivatized with diazomethane, evaporated and taken up in 20 µL dichloromethane (Sigma) followed by GC-MS analysis.

Characterization of Purified Recombinant AaALDH1

The linearity of the assay with respect to time and protein concentration was first established and the operational saturation of substrate and cofactor determined. The pH optimum was determined by the standard assay in 50 mM buffer (sodium phosphate, Tris-HCl and CHES) from pH 6.0 to 10.0 at 0.5 unit interval containing 1 mM NADP and 1.5 micrograms of the purified recombinant AaALDH1. Kinetic parameters were determined in 50 mM Tris-HCl buffer, pH 8.5 by varying the concentration of the substrates. Kinetic constants were determined by non-linear regression analysis using GraphPad software (GraphPad Software Inc. San Diego, Calif.) and the results presented are the means of three independent experiments. Substrates specificity was determined at optimum reaction conditions with substrates concentration at 10 times the estimated Km value. Substrates tested include artemisinic aldehyde, (11R)-dihydroartemisinic aldehyde, artemisinic alcohol, dihydroartemisinic alcohol, octanal, nonanal, 2-phenyl propionaldehyde, 3-cyclohexyl propionaldehyde, 2-hexen-1-al, syringaldehyde.

Results:

Expressed sequence tags (sequences of randomly picked cDNA clones) were generated from developing trichomes and flower buds of *Artemisia annua* and analyzed.

cDNA clones with sequences similar to monoterpene double-bond reductases were resequenced and these sequences were assembled. These were deemed to be derived from a single *Artemisia annua* gene which was called AaDBR1. The consensus nucleotide sequence of the AaDBR1 mRNA is shown in FIG. 2 (SEQ ID No.: 1). The corresponding amino acid sequence is shown in FIG. 3 (SEQ ID No.: 2).

cDNA clones with sequences similar to aldehyde dehydrogenase were resequenced and these sequences were assembled. These were deemed to be derived from a single *Artemisia annua* gene which was called AaALDH1. The consensus nucleotide sequence of the AaALDH1 mRNA is shown in FIG. 6 (SEQ ID No.: 5). The corresponding amino acid sequence is shown in FIG. 7 (SEQ ID No.: 6).

Figure 10:
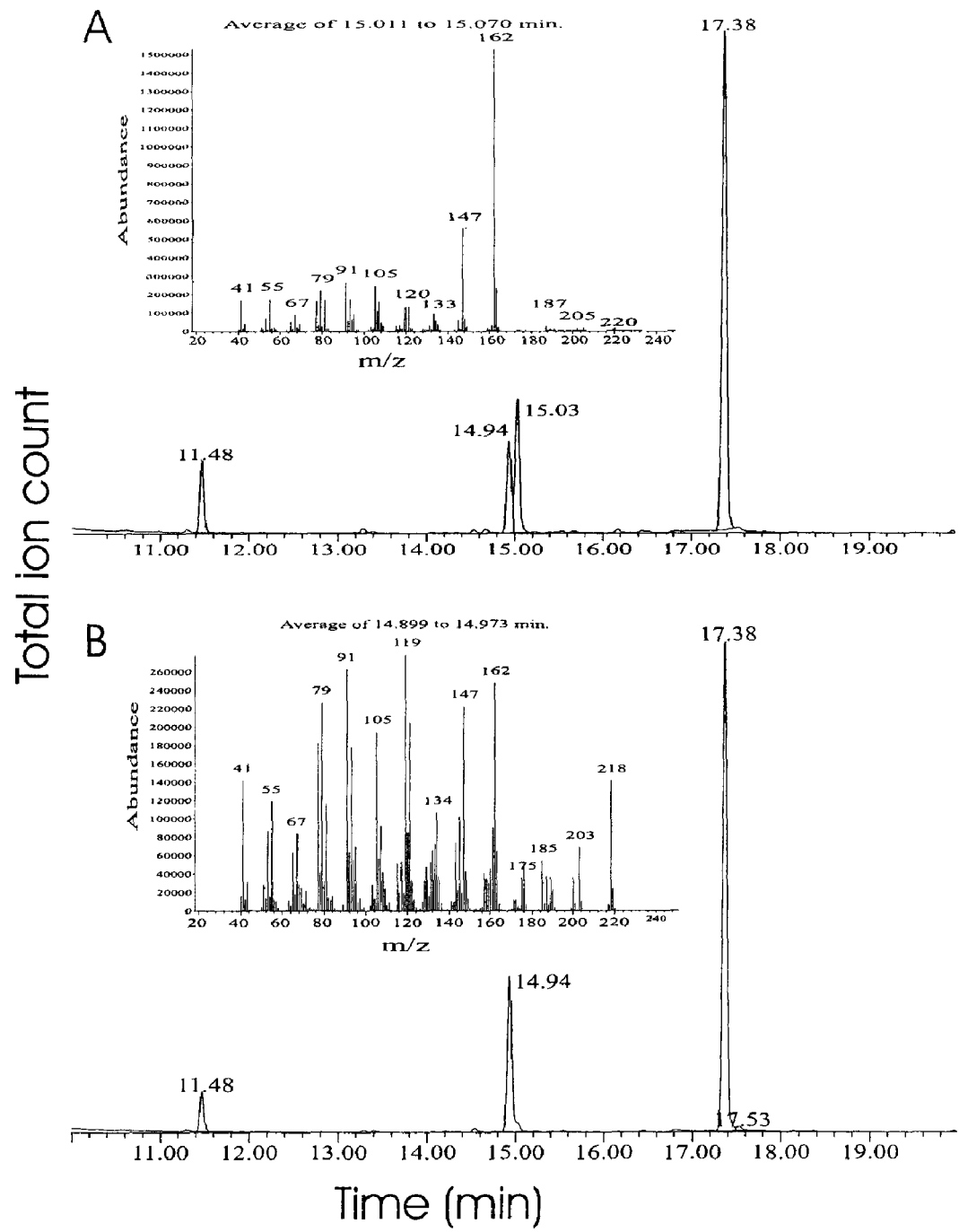
FIG. 10 depicts a GC/MS of E. coli cell free extracts expressing AaDBR1 tested with artemisinic aldehyde with (a) and without (b) added NADPH. The retention time and mass spectrum of the peaks at 14.94 and 15.03 min are equivalent to the standard artemisinic aldehyde ($M_r^+$ 218) and (11S)-dihydroartemisinic aldehyde ($M_r^+$ 220), respectively.

For initial functional studies of AaDBR1, an RT-PCR product was prepared and cloned into *E. coli* expression vector pDEST17 to give the clone pKT032. The nucleotide sequence of the open reading frame of the DNA insert of pKT032 is given in FIG. 4 (SEQ ID No.: 3) and the corresponding protein product including the N-terminal His tag fusion is given in FIG. 5 (SEQ ID No.: 4). The plasmid pKT032 was introduced into the *E. coli* (DE3) strain (Novagen) and cell-free extracts was assayed with various isoprenoid substrates followed by analysis by gas chromatography/mass spectrometry. FIG. 10 shows the results of this analysis indicating the NADPH-dependent formation of (11S)-dihydroartemisinic aldehyde as the major product. In a separate experiment, extracts from *E. coli* into which pKT032 had not been introduced did not support the production of dihydroartemisinic aldehyde in the presence of NADPH. It is predicted that the wild type product of AaDBR1 will have similar artemisinic aldehyde double bond reductase activity as the His tag fusion protein product of pKT032.

Figure 11:
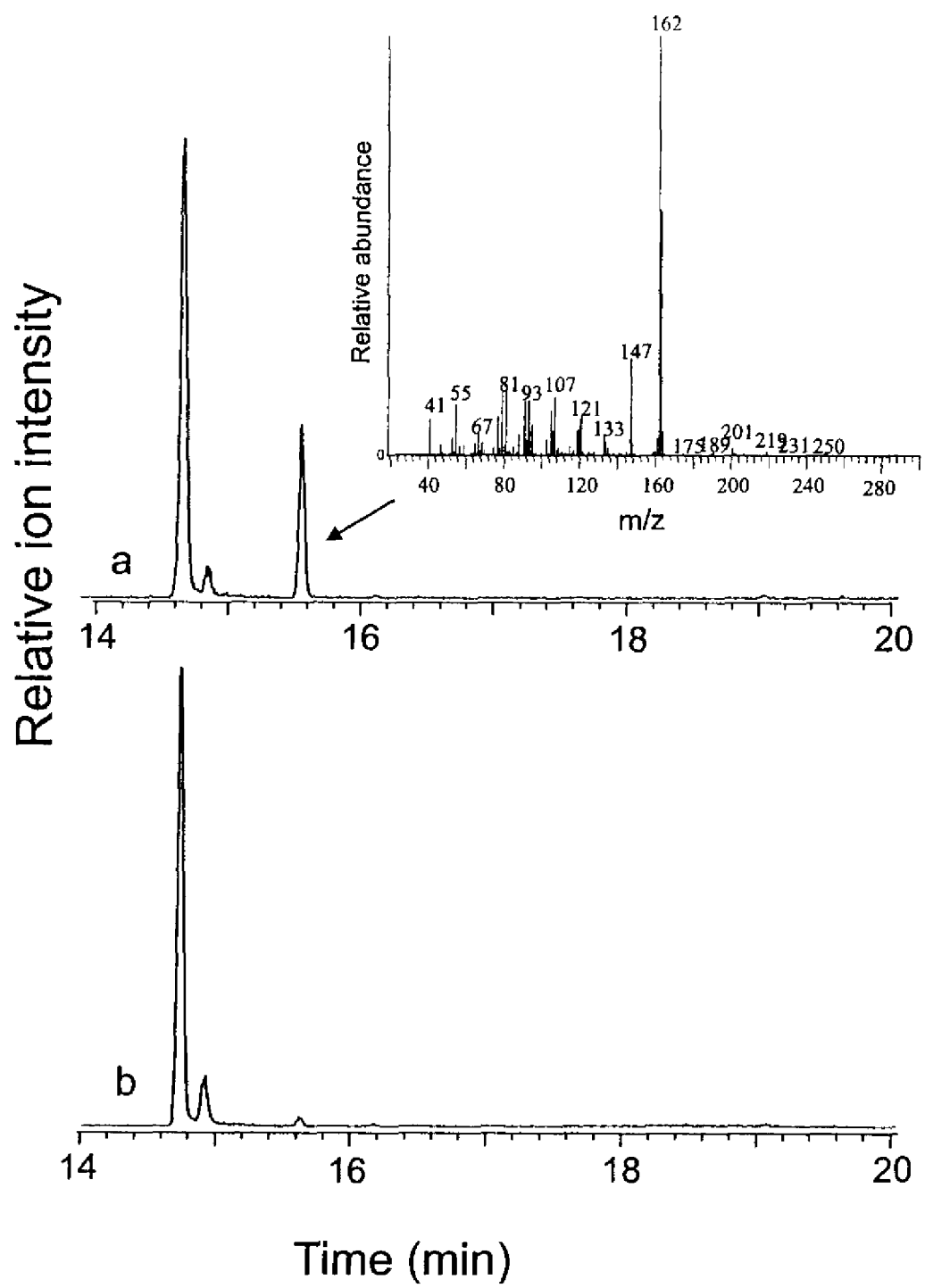
FIG. 11 depicts a GC/MS of E. coli cell free extracts expressing AaALDH1 tested with (11R)-dihydroartemisinic aldehyde with (a) and without (b) added NADP. Diethyl ether extracts were analyzed as diazomethane derivatives. The retention time and mass spectrum of the peak at 15.8 min is equivalent to the standard diazomethane derivative of (11R)-dihydroartemisinic acid ($M^+$ 250).

For initial functional studies of AaALDH1, a PCR product was prepared and cloned into *E. coli* expression vector pDEST17 to give the clone pKT041. The nucleotide sequence of the open reading frame of the DNA insert of pKT041 is given in FIG. 8 (SEQ ID No.: 7) and the corresponding protein product including the N-terminal His tag fusion is given in FIG. 9 (SEQ ID No.: 8). The plasmid pKT041 was introduced into the *E. coli* (DE3) strain (Novagen) and cell-free extracts was assayed with (11R)-dihydroartemisinic aldehyde followed by analysis by gas chromatography/mass spectrometry. The recombinant AaALDH1 protein was purified from the cell-free extract and its kinetic parameters were determined. The purified recombinant AaALDH1 protein functions best at pH 8.5. The recombinant protein was tested with different substrates (see Materials and Methods) at the optimum assay conditions. Artemisinic aldehyde besides (11R)-dihydroartemisinic aldehyde was found to be a substrate for the recombinant AaALDH1. The $K_m$ and $V_{max}$ values determined for dihydroartemisinic acid were 8.79 µM and 143.8 pkat/µg protein, respectively and for artemisinic aldehyde the Km and $V_{max}$ were 2.62 µM and 28.6 pkat/µg protein, respectively. FIG. 11 shows the results of the analysis for (11R)-dihydroartemisinic aldehyde indicating the NADP-dependent formation of dihydroartemisinic acid. In separate experiment, extracts from *E. coli* into which pKT041 had not been introduced did not support the production of dihydroartemisinic acid in the presence of NADP. It is predicted that the wild type product of AaALDH1 will have similar artemisinic/dihydroartemisinic aldehyde dehydrogenase activity as the His-tag fusion protein product of pKT041.

REFERENCES

The disclosures of the following references are incorporated herein by reference in their entirety.

Altschul, S. F., Gish, W., Miller, W., Myers, E., & Lipman, D. J. 1990, "Basic local alignment search tool", *Journal of Molecular Biology*, vol. 215, pp. 403-410.

Bagge, M., Xia, X., & Lubberstedt, T. 2007, "Functional markers in wheat", *Curr. Opin. Plant Biol.*, vol. 10, no. 2, pp. 211-216.

Bertea, C. M., Freije, J. R., van der, W. H., Verstappen, F. W., Perk, L., Marquez, V., de Kraker, J. W., Posthumus, M. A., Jansen, B. J., de Groot, A., Franssen, M. C., & Bouwmeester, H. J. 2005, "Identification of intermediates and enzymes involved in the early steps of artemisinin biosynthesis in *Artemisia annua*", *Planta Med.*, vol. 71, no. 1, pp. 40-47.

Bouwmeester, H. J., Wallaart, E. T., Janssen, M. H., van Loo, B., Jansen, B. J. M., Posthumus, M. A., Schmidt, C. O., De Kraker, J.-W., Konig, W. A., & Franssen, M. C. R. 1999, "Amorpha-4,11-diene synthase catalyses the first probable step in artemisinin biosynthesis", *Phytochemistry*, vol. 52, pp. 843-854.

Cahoon, E. B., Carlson, T. J., Ripp, K. G., Schweiger, B. J., Cook, G. A., Hall, S. E., & Kinney, A. J. 1999, "Biosynthetic origin of conjugated double bonds: production of fatty acid components of high-value drying oils in transgenic soybean embryos", *Proceedings of the National Academy of Sciences (U.S.A.)*, vol. 96, pp. 12935-12940.

Chang, Y. J., Song, S. H., Park, S. H., & Kim, S. U. 2000, "Amorpha-4,11-diene synthase of *Artemisia annua*: cDNA isolation and bacterial expression of a terpene synthase involved in artemisinin biosynthesis", *Archives of Biochemistry and Biophysics*, vol. 383, no. 2, pp. 178-184.

Chou, H.-H. & Holmes, M. H. 2001, "DNA sequence quality trimming and vector removal", *Bioinformatics*, vol. 17, pp. 1093-1104.

Comai, L. & Henikoff, S. 2006, "TILLING: practical single-nucleotide mutation discovery", *Plant J.*, vol. 45, no. 4, pp. 684-694.

Corey, E. J., & Suggs, J. W. 1975, "Pyridinium Chlorochromate: An efficient reagent for oxidation of primary and secondary alcohols to carbonyl compounds", *Tetrahedron Lett.* vol. 31, pp. 2647-2650.

Duke, S. O. & Paul, R. N. 1993, "Development and fine structure of the glandular trichomes of *Artemisia annua* L.", *Int. J. Plant Sci.*, vol. 154, pp. 107-118.

Duke, M. V., Paul, R. N., Elsohly, H. N., Sturtz, G., & Duke, S. O. 1994, "Localization of artemisinin and artemisitene in foliar tisuues of glanded and glandless biotypes of *artemisia annua*", *Int. J. Plant Sci.*, vol. 155, pp. 365-372.

Elferaly, F. S. 1990, Method for the isolation of artemisinin from *Artemisia annua*, U.S. Pat. No. 4,952,603.

Ewing, B., Hillier, L., Wendl, M. C., & Green, P. 1998, "Base-calling of automated sequencer traces using phred I. Accuracy assessment", *Genome Res.*, vol. 8, pp. 175-185.

Gang, D. R., Wang, J., Dudareva, N., Nam, K. H., Simon, J. E., Lewinsohn, E., & Pichersky, E. 2001, "An investigation of the storage and biosynthesis of phenylpropenes in sweet basil", *Plant Physiol*, vol. 125, no. 2, pp. 539-555.

Gupta, S. K., Singh, P., Bajpai, P., Ram, G., Singh, D., Gupta, M. M., Jain, D. C., Khanuja, S. P., & Kumar, S. 2002, "Morphogenetic variation for artemisinin and volatile oil in *Atemisia annua*", *Ind Crops Products*, vol. 16, pp. 217-224.

Henikoff S, Till B J, Comai L (2004). "TILLING. Traditional mutagenesis meets functional genomics", *Plant Physiol* 135:630-6.

Jung, M., Lee, K., & Jung, H. 2001, "First synthesis of (+)-deoxyartemisitene and its novel C-11 derivatives", *Tetrahedron Lett*, vol. 42, pp. 3997-4000.

Keasling et al., 2007, Biosynthesis of isopentenyl pyrophosphate, U.S. Pat. No. 7,172,886 issued Feb. 6, 2007.

Konieczny, A., Ausubel, F. M. 1993, "A procedure for mapping Arabidopsis mutations using co-dominant ecotype-specific PCR-based markers", *The Plant Journal* 4 (2), 403-410.

Kumar, S. 2002, Method for maximization of artemisinin production by plant artemisisa annua, U.S. Pat. No. 6,393,763 issued May 28, 2002.

Lange, B. M., Wildung, M. R., Stauber, E. J., Sanchez, C., Pouchnik, D., & Croteau, R. 2000, "Probing essential oil biosynthesis and secretion by functional evaluation of expressed sequence tags from mint glandular trichomes", *Proc. Natl. Acad. Sci. U.S.A*, vol. 97, no. 6, pp. 2934-2939.

Logemann, J., Schell, J., & Willmitzer, L. 1987, "Improved method for the isolation of RNA from plant tissues", *Analytical Biochemistry*, vol. 163, pp. 16-20.

Martin, V. J., Pitera, D. J., Withers, S. T., Newman, J. D., & Keasling, J. D. 2003, "Engineering a mevalonate pathway in Escherichia coli for production of terpenoids", *Nat. Biotechnol.*, vol. 21, no. 7, pp. 796-802.

Miller, R. T., Christoffels, A. G., Gopalakrishnan, C., Burke, J., Ptitsyn, A. A., Broveak, T. R., & Hide, W. A. 1999, "A comprehensive approach to clustering of expressed human gene sequence: the sequence tag alignment and consensus knowledge base", *Genome Res.*, vol. 9, no. 11, pp. 1143-1155.

O'Neill, P. M. 2005, "The therapeutic potential of semi-synthetic artemisinin and synthetic endoperoxide antimalarial agents", *Expert. Opin. Investig. Drugs*, vol. 14, no. 9, pp. 1117-1128.

Pfaff, T. & Kahl, G. 2003, "Mapping of gene-specific markers on the genetic map of chickpea (Cicer arietinum L.)", *Mol. Genet. Genomics*, vol. 269, no. 2, pp. 243-251.

Rathore, D., McCutchan, T. F., Sullivan, M., & Kumar, S. 2005, "Antimalarial drugs: current status and new developments", *Expert. Opin. Investig. Drugs*, vol. 14, no. 7, pp. 871-883.

Ringer, K. L., McConkey, M. E., Davis, E. M., Rushing, G. W., & Croteau, R. 2003, "Monoterpene double-bond reductases of the (-)-menthol biosynthetic pathway: isolation and characterization of cDNAs encoding (-)-isopiperitenone reductase and (+)-pulegone reductase of peppermint", *Arch. Biochem. Biophys.*, vol. 418, pp. 80-92.

Ro, D. K., Paradise, E. M., Ouellet, M., Fisher, K. J., Newman, K. L., Ndungu, J. M., Ho, K. A., Eachus, R. A., Ham, T. S., Kirby, J., Chang, M. C., Withers, S. T., Shiba, Y., Sarpong, R., & Keasling, J. D. 2006, "Production of the antimalarial drug precursor artemisinic acid in engineered yeast", *Nature*, vol. 440, no. 7086, pp. 940-943.

Robert, A., Coppel, Y., & Meunier, B. 2002, "Alkylation of heme by the antimalarial drug artemisinin", *Chem. Commun. (Camb.)* no. 5, pp. 414-415.

Rotheim, P. 2002, *Plant-Derived Drugs: Products, Technologies and Applications*, Business Communications Co., Norwalk, B-121.

Sandal, N., Krusell, L., Radutoiu, S., Olbryt, M., Pedrosa, A., Stracke, S., Sato, S., Kato, T., Tabata, S., Parniske, M., Bachmair, A., Ketelsen, T., & Stougaard, J. 2002, "A genetic linkage map of the model legume Lotus japonicus and strategies for fast mapping of new loci", *Genetics*, vol. 161, no. 4, pp. 1673-1683.

Schwikkard, S. & van Heerden, F. R. 2002, "Antimalarial activity of plant metabolites", *Natural Product Reports*, vol. 19, no. 6, pp. 675-692.

Slade, A. J. & Knauf, V. C. 2005, "TILLING moves beyond functional genomics into crop improvement", *Transgenic Res.*, vol. 14, no. 2, pp. 109-115.

Stone, R. T., Grosse, W. M., Casas, E., Smith, T. P., Keele, J. W., & Bennett, G. L. 2002, "Use of bovine EST data and human genomic sequences to map 100 gene-specific bovine markers", *Mammalian Genome*, vol. 13, no. 4, pp. 211-215.

Sy, L.-K. & Brown, G. D. 2002, "The mechanism of the spontaneous autoxidation of dihydroartemisinic acid", *Tetrahedron*, vol. 58, pp. 897-908.

Teoh, K. H., Polichuk, D. R., Reed, D. W., Nowak, G., & Covello, P. S. 2006, "*Artemisia annua* L. (Asteraceae) trichome-specific cDNAs reveal CYP71AV1, a cytochrome P450 with a key role in the biosynthesis of the antimalarial sesquiterpene lactone artemisinin", *FEBS Letters*, vol. 580, no. 5, pp. 1411-1416.

Torrell, M., Garcia-Jacas, N., Susanna, A., & Valles, J. 1999, "Phylogeny in *Artemisia* (Asteraceae, Anthemideae) inferred from nuclear ribosomeal DNA (ITS) sequences", *Taxon*, vol. 48, p. 721.

van Agtmael, M. A., Eggelte, T. A., & van Boxtel, C. J. 1999b, "Artemisinin drugs in the treatment of malaria: from medicinal herb to registered medication", *Trends Pharmacol. Sci.*, vol. 20, no. 5, pp. 199-205.

van Agtmael, M. A., Eggelte, T. A., & van Boxtel, C. J. 1999a, "Artemisinin drugs in the treatment of malaria: from medicinal herb to registered medication", *Trends Pharmacol Sci.*, vol. 20, no. 5, pp. 199-205.

van de Loo, F. J., Turner, S., & Somerville, C. 1995, "Expressed sequence tags from developing castor seeds", *Plant Physiology*, vol. 108, pp. 1141-1150.

Wallaart et al., 2006, *Transgenic amorpha-4,11-diene synthesis*, U.S. Pat. No. 7,091,027 issued Aug. 15, 2006.

Wallaart, T. E., Bouwmeester, H. J., Hille, J., Poppinga, L., & Maijers, N. C. A. 2001, "Amorpha-4,11-diene synthase: cloning and functional expression of a key enzyme in the biosynthetic pathway of the novel antimalarial drug artemisinin", *Planta*, vol. 212, pp. 460-465.

Wallaart, T. E., Van Uden, W., Lubberink, H. G. M., Woerdenbag, H. J., Pras, N., & Quax, W. J. 1999, "Isolation and identification of dihydroartemisinic acid from *Artemisia annua* and its possible role in the biosynthesisi of artemisinin.", *J Nat Prod*, vol. 62, pp. 430-433.

Watson, L. E., Evans, T. M., & Boluarte, T. 2000, "Molecular phylogeny and biogeography of tribe Anthemideae (Asteraceae), based on chloroplast ndhF", *Mol. Phylogen. Evol.*, vol. 15, pp. 59-69.

Wilairatana, P., Krudsood, S., Treeprasertsuk, S., Chalermrut, K., & Looareesuwan, S. 2002, "The future outlook of antimalarial drugs and recent work on the treatment of malaria", *Arch. Med. Res.*, vol. 33, no. 4, pp. 416-421.

Wu, Y. 2002, "How might qinghaosu (artemisinin) and related compounds kill the intraerythrocytic malaria parasite? A chemist's view", *Acc. Chem. Res.*, vol. 35, no. 5, pp. 255-259.

Yadav, J. S., Babu, R. S., & Sabitha, G. 2003, "Stereoselective total synthesis of (+)-artemisinin", *Tetrahedron Lett*, vol. 44, pp. 387-389.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. Isolated nucleic acid molecule comprising the nucleotide sequence as set forth in SEQ ID No.: 7 and encoding an artemisinic/dihydroartemisinic aldehyde dehydrogenase.

2. Isolated nucleic acid molecule comprising a nucleotide sequence encoding an artemisinic/dihydroartemisinic aldehyde dehydrogenase having the amino acid sequence as set forth in SEQ ID No.: 6.

3. The isolated nucleic acid molecule of claim 1 comprising the nucleotide sequence as set forth in SEQ ID No.: 5.

4. Purified artemisinic/dihydroartemisinic aldehyde dehydrogenase comprising the amino acid sequence as set forth in SEQ ID No.: 6.

5. A method of selecting or developing plants with altered dihydroartemisinic aldehyde, dihydroartemisinic acid, artemisinic acid and/or artemisinin levels in a population of plants that naturally produces dihydroartemisinic aldehyde, dihydroartemisinic acid, artemisinic acid and/or artemisinin comprising:
   detecting a target plant having altered levels of dihydroartemisinic aldehyde, dihydroartemisinic acid, artemisinic acid and/or artemisinin compared to a control plant provided under similar conditions;
   isolating at least a portion of an artemisinic/dihydroartemisinic aldehyde dehydrogenase gene of the target plant and comparing the nucleotide sequence of the at least a portion to SEQ ID No. 5 or SEQ ID No. 7 to detect a variation from SEQ ID No. 5 or SEQ ID No. 7;
   detecting the variation in other plants;
   selectively breeding the plants with the variation to produce a population of plants having altered levels of dihydroartemisinic aldehyde, dihydroartemisinic acid, artemisinic acid and/or artemisinin compared to a population of control plants produced under similar conditions.

6. A method of altering dihydroartemisinic aldehyde, dihydroartemisinic acid, artemisinic acid and/or artemisinin levels in a population of plants that naturally produces dihydroartemisinic aldehyde, dihydroartemisinic acid and/or artemisinic acid comprising:
   providing a population of mutated plants;
   detecting a target mutated plant within the population of mutated plants, the target mutated plant having an altered expression of an artemisinic/dihydroartemisinic aldehyde dehydrogenase gene or altered activity of an artemisinic/dihydroartemisinic aldehyde dehydrogenase enzyme compared to a control plant provided under similar conditions,
   said detecting comprising using primers developed from a nucleic acid molecule as defined in claim 1 to PCR amplify regions of the artemisinic/dihydroartemisinic aldehyde dehydrogenase gene from mutated plants in the population of mutated plants, identifying mismatches between the amplified regions and corresponding regions in wild-type gene that lead to the altered expression or altered activity, and identifying the mutated plant that contains the mismatches; and,
   selectively breeding the target mutated plant to produce a population of plants having altered expression of artemisinic/dihydroartemisinic aldehyde dehydrogenase gene or altered activity of artemisinic/dihydroartemisinic aldehyde dehydrogenase enzyme compared to a population of control plants produced under similar conditions.

7. The isolated nucleic acid molecule of claim 1 derived from *Artemisia annua*.

8. Process for producing dihydroartemisinic acid and/or artemisinic acid comprising expressing or overexpressing the isolated nucleic acid molecule of claim 2 in a host cell.

9. The process of claim 8, further comprising expressing or overexpressing in the host cell one or more nucleic acid molecules encoding amorpha-4,11-diene synthase and/or amorpha-4,11-diene hydroxylase.

10. The process of claim 8, wherein the host cell is a plant cell, a yeast cell or a bacterial cell.

* * * * *

SEQUENCE LISTING

<160> NUMBER OF SEQ ID NOS: 13

<210> SEQ ID NO 1
<211> LENGTH: 1296
<212> TYPE: DNA
<213> ORGANISM: Artemisia annua

<400> SEQUENCE: 1

```
gactttttaa atccacctct tcaaccttca aaactcaaag aacatttca acatggaaca      60
gcaacaagaa gtgatcacca acaagaaagt aatactaaaa gactacgttg tagggtttcc     120
taaggagtcc gacatgatcc ttaaaacatc tgaaaccatg acactgaagc ttccagcagg     180
ttctaatggt ttacttgtta agaatcttta tttgtcgtgt gatccttaca tgcgttctcg     240
catgactaaa actgaaggca gttatgtcga gtcttttact cctggttcgc ctctaacagg     300
atatggagta gctaaggttc ttgaatctgg gcatgcaaac tttaagaaag gcgacctaat     360
ttggggattt acaggatggg aagagtacag cattatcaat gctcctgagg gtctattcaa     420
gattgaacat accgatgtgc ctctttctta ttatacagga attcttggta tgcctggcat     480
gactgcttat gttggtttct atgagatatg tactccaaaa aaaggagagt atgtctttgt     540
ttcggctgct tctggtgcag ttgggcagct ggttgggcag tttgctaagt tgtccggatg     600
ctatgttgtt gggagtgctg gtacgaagga aaaggttgat ttgctgaaga acaaatttgg     660
atttgatgaa gcttttaatt acaaggaaga gcaagatctg gatgcggctc tgaagaggta     720
ctttcccgaa ggaattgata tttactttga gaacgttgga ggaaggatgt tggatgcagt     780
actcttgaac atgagactag atggccgaat ttcagtttgt ggtatgatct cacaatacaa     840
cttagagcaa tctgagggag tgcgtaacct cttcaccctc gtaacaaaac gtgtgaccat     900
gaaagggttc attgtgtttg atcactatca caagtaccca aagtatctag aaatgattat     960
accctaatt aaaaatggca cgataaatta catagaagac attgtagaag ggctcgagaa    1020
tgcacccgcg gctttgattg gtctgtattc tggaaaaaat gttggaaagc aagtggtggt    1080
ggttgcgcat gaatgatgaa gagttaaggc taaatggtgg tactatgaat acttttagg     1140
tttgattttg gtcagagtgt gggattgtat ggaataaatt tctccaagtt ctaatactta    1200
gggggtgttt gatttcgact taatatgaaa aaaattaaat taattaagtc atatgaaaac    1260
tgtttgtttg tgactgaaaa aaaaaaaaaa aaaaaa                              1296
```

<210> SEQ ID NO 2
<211> LENGTH: 347
<212> TYPE: PRT
<213> ORGANISM: Artemisia annua

<400> SEQUENCE: 2

Met Glu Gln Gln Gln Glu Val Ile Thr Asn Lys Lys Val Ile Leu Lys

```
              1               5                  10                 15
Asp Tyr Val Val Gly Phe Pro Lys Glu Ser Asp Met Ile Leu Lys Thr
                20                  25                  30

Ser Glu Thr Met Thr Leu Lys Leu Pro Ala Gly Ser Asn Gly Leu Leu
            35                  40                  45

Val Lys Asn Leu Tyr Leu Ser Cys Asp Pro Tyr Met Arg Ser Arg Met
 50                  55                  60

Thr Lys Thr Glu Gly Ser Tyr Val Glu Ser Phe Thr Pro Gly Ser Pro
 65                  70                  75                  80

Leu Thr Gly Tyr Gly Val Ala Lys Val Leu Glu Ser Gly His Ala Asn
                85                  90                  95

Phe Lys Lys Gly Asp Leu Ile Trp Gly Phe Thr Gly Trp Glu Glu Tyr
                100                 105                 110

Ser Ile Ile Asn Ala Pro Glu Gly Leu Phe Lys Ile Glu His Thr Asp
            115                 120                 125

Val Pro Leu Ser Tyr Tyr Thr Gly Ile Leu Gly Met Pro Gly Met Thr
            130                 135                 140

Ala Tyr Val Gly Phe Tyr Glu Ile Cys Thr Pro Lys Lys Gly Glu Tyr
145                 150                 155                 160

Val Phe Val Ser Ala Ala Ser Gly Ala Val Gly Gln Leu Val Gly Gln
                165                 170                 175

Phe Ala Lys Leu Ser Gly Cys Tyr Val Val Gly Ser Ala Gly Thr Lys
            180                 185                 190

Glu Lys Val Asp Leu Leu Lys Asn Lys Phe Gly Phe Asp Glu Ala Phe
            195                 200                 205

Asn Tyr Lys Glu Glu Gln Asp Leu Asp Ala Ala Leu Lys Arg Tyr Phe
210                 215                 220

Pro Glu Gly Ile Asp Ile Tyr Phe Glu Asn Val Gly Gly Arg Met Leu
225                 230                 235                 240

Asp Ala Val Leu Leu Asn Met Arg Leu Asp Gly Arg Ile Ser Val Cys
                245                 250                 255

Gly Met Ile Ser Gln Tyr Asn Leu Glu Gln Ser Glu Gly Val Arg Asn
                260                 265                 270

Leu Phe Thr Leu Val Thr Lys Arg Val Thr Met Lys Gly Phe Ile Val
            275                 280                 285

Phe Asp His Tyr His Lys Tyr Pro Lys Tyr Leu Glu Met Ile Ile Pro
            290                 295                 300

Leu Ile Lys Asn Gly Thr Ile Asn Tyr Ile Glu Asp Ile Val Glu Gly
305                 310                 315                 320

Leu Glu Asn Ala Pro Ala Ala Leu Ile Gly Leu Tyr Ser Gly Lys Asn
                325                 330                 335

Val Gly Lys Gln Val Val Val Ala His Glu
            340                 345

<210> SEQ ID NO 3
<211> LENGTH: 1128
<212> TYPE: DNA
<213> ORGANISM: Artemisia annua

<400> SEQUENCE: 3
atgtcgtact accatcacca tcaccatcac ctcgaatcaa caagtttgta caaaaaagca      60
ggctccgcgg ccgccccctt caccatggaa cagcaacaag aagtgatcac caacaagaaa     120
gtaatactaa aagactacgt tgtagggttt cctaaggagt ccgacatgat ccttaaaaca     180
tctgaaacca tgacactgaa gcttccagca ggttctaatg gtttacttgt taagaatctt     240
```

```
tatttgtcgt gtgatcctta catgcgttct cgcatgacta aaactgaagg cagttatgtc      300
gagtctttta ctcctggttc gcctctaaca ggatatggag tagctaaggt tcttgaatct      360
gggcatgcaa actttaagaa aggcgaccta atttggggat ttacaggatg ggaagagtac      420
agcattatca atgctcctga gggtctattc aagattgaac ataccgatgt gcctctttct      480
tattatacag gaattcttgg tatgcctggc atgactgctt atgttggttt ctatgagata      540
tgtactccaa aaaaggaga gtatgtcttt gtttcggctg cttctggtgc agttgggcag      600
ctggttgggc agtttgctaa gttgtccgga tgctatgttg ttgggagtgc tggtacgaag      660
gaaaaggttg atttgctgaa gaacaaattt ggatttgatg aagcttttaa ttacaaggaa      720
gagcaagatc tggatgcggc tctgaagagg tactttcccg aaggaattga tatttacttt      780
gagaacgttg gaggaaggat gttggatgca gtactcttga acatgagact agatggccga      840
atttcagttt gtggtatgat ctcacaatac aacttagagc aatctgaggg agtgcgtaac      900
ctcttcaccc tcgtaacaaa acgtgtgacc atgaaagggt tcattgtgtt tgatcactat      960
cacaagtacc caaagtatct agaaatgatt ataccccctaa ttaaaaatgg cacgataaat     1020
tacatagaag acattgtaga agggctcgag aatgcacccg cggctttgat tggtctgtat     1080
tctggaaaaa atgttggaaa gcaagtggtg gtggttgcgc atgaatga                  1128
```

<210> SEQ ID NO 4
<211> LENGTH: 375
<212> TYPE: PRT
<213> ORGANISM: Artemisia annua

<400> SEQUENCE: 4

```
Met Ser Tyr Tyr His His His His His His Leu Glu Ser Thr Ser Leu
1               5                   10                  15

Tyr Lys Lys Ala Gly Ser Ala Ala Pro Phe Thr Met Glu Gln Gln
            20                  25                  30

Gln Glu Val Ile Thr Asn Lys Lys Val Ile Leu Lys Asp Tyr Val Val
        35                  40                  45

Gly Phe Pro Lys Glu Ser Asp Met Ile Leu Lys Thr Ser Glu Thr Met
    50                  55                  60

Thr Leu Lys Leu Pro Ala Gly Ser Asn Gly Leu Leu Val Lys Asn Leu
65                  70                  75                  80

Tyr Leu Ser Cys Asp Pro Tyr Met Arg Ser Arg Met Thr Lys Thr Glu
                85                  90                  95

Gly Ser Tyr Val Glu Ser Phe Thr Pro Gly Ser Pro Leu Thr Gly Tyr
            100                 105                 110

Gly Val Ala Lys Val Leu Glu Ser Gly His Ala Asn Phe Lys Lys Gly
        115                 120                 125

Asp Leu Ile Trp Gly Phe Thr Gly Trp Glu Glu Tyr Ser Ile Ile Asn
    130                 135                 140

Ala Pro Glu Gly Leu Phe Lys Ile Glu His Thr Asp Val Pro Leu Ser
145                 150                 155                 160

Tyr Tyr Thr Gly Ile Leu Gly Met Pro Gly Met Thr Ala Tyr Val Gly
                165                 170                 175

Phe Tyr Glu Ile Cys Thr Pro Lys Lys Gly Glu Tyr Val Phe Val Ser
            180                 185                 190

Ala Ala Ser Gly Ala Val Gly Gln Leu Val Gly Gln Phe Ala Lys Leu
        195                 200                 205

Ser Gly Cys Tyr Val Val Gly Ser Ala Gly Thr Lys Glu Lys Val Asp
    210                 215                 220
```

```
Leu Leu Lys Asn Lys Phe Gly Phe Asp Glu Ala Phe Asn Tyr Lys Glu
225                 230                 235                 240

Glu Gln Asp Leu Asp Ala Ala Leu Lys Arg Tyr Phe Pro Glu Gly Ile
            245                 250                 255

Asp Ile Tyr Phe Glu Asn Val Gly Gly Arg Met Leu Asp Ala Val Leu
        260                 265                 270

Leu Asn Met Arg Leu Asp Gly Arg Ile Ser Val Cys Gly Met Ile Ser
    275                 280                 285

Gln Tyr Asn Leu Glu Gln Ser Glu Gly Val Arg Asn Leu Phe Thr Leu
290                 295                 300

Val Thr Lys Arg Val Thr Met Lys Gly Phe Ile Val Phe Asp His Tyr
305                 310                 315                 320

His Lys Tyr Pro Lys Tyr Leu Glu Met Ile Ile Pro Leu Ile Lys Asn
                325                 330                 335

Gly Thr Ile Asn Tyr Ile Glu Asp Ile Val Glu Gly Leu Glu Asn Ala
            340                 345                 350

Pro Ala Ala Leu Ile Gly Leu Tyr Ser Gly Lys Asn Val Gly Lys Gln
        355                 360                 365

Val Val Val Val Ala His Glu
370                 375

<210> SEQ ID NO 5
<211> LENGTH: 1786
<212> TYPE: DNA
<213> ORGANISM: Artemisia annua

<400> SEQUENCE: 5
tgactcacta tagggcgct  agctcgccgc agccgaacga ccgagcgcag cgagtcagtg      60
agcgaggaag cggccgcata acttcgtata gcatacatta gattcgaccc ttgaataaaa    120
atttcataaa aaacaaagat gagctcagga gctaatggaa gttctaagtc agcaagccat    180
aaaatcaagt tcaccaagct tttatcaat  ggcgaatttg ttgattctat ttcaggaaac    240
acttttgaca cgattaatcc agcgacagaa gaagtgttag caacagtggc cgaaggaaga    300
aaggaagaca ttgatttggc cgttaaggct gcccgtgaag ctttcgacaa tggaccttgg    360
cctcgcatgt ctggcgaggc acgccgaaaa atcatgttaa agttcgcaga cttgatcgat    420
gaaaatgctg acgagttaac caccttagaa gtaatcgatg aggaaaatt  gtttggccca    480 gtgaggcact tgaagtccc  ggtttcatca gatacatttc gttactttgc gggtgcagcc    540
gataaaatcc gtggagcaac tcttaaaatg tcaagtaata ttcaagctta tacgctacgt    600
gaacccatcg gagtagttgg tcacatcatt ccttggaatg tcctgccttc atgttcgct    660 acaaaggttg caccagcttt agctgctggc tgcaccatgg tcatcaagcc tgccgaacat    720
actcccctta cagttctctt tttagctcac ctgtcgaagc tggctggtgt tcctgatggc    780
gtgattaatg tggttaacgg gtttggaaaa actgctggtc tgccgttag  ctcgcatatg    840 gacattgaca tggttacttt tacgggatcc acagaagttg gccgcaccgt aatgcaagct    900
gcagctctaa gtaatctgaa accagtgtca ctcgaacttg gaggaaaatc gcctttgatt    960
gttttcgatg atgcagatgt tgataaagcc gcagaatttg ctattttggg aaattttact   1020
aacaaaggtg agatgtgtgt ggcagggtct cgtgttttcg ttcaggaagg gatccatgac   1080
gtattcgtaa aaaaattgga aggagcggtg aaagcgtggg caacaaggga cccttttgat   1140
ctcgccactc gtcatggacc tcagaataac aaacaacaat atgataaagt acttcatgc    1200 atcaaccatg gcaaaaagga aggtgcgact ttggtaaccg gtggtaagcc atttgggaag   1260
```

```
aaaggatact acattgagcc tactctattt acaaacgtta cggatgatat gaccatagca   1320
aaggaagaaa ttttggcccc cgttatatct gttctcaagt tcaagactgt tgaagaagtg   1380
attaaaagag caaatgccac aaaatatgga cttgcctcag gtgtattcac caaaaatatt   1440
gatgtcgtga acacagtttc gagatctatt cgagcaggtg ctgtttgggt caactgttat   1500
ttagcactcg accgggatgc acctcatgga gggtataaaa tgagtggggtt tggacgagaa   1560 caaggattag aggcacttga acattatctt cagattaaga cagtggctac acccatatat   1620
gattccccgt ggctctaaac tttcatattt gtttgtttat caaataagaa gactgcggtc   1680
catttatcga atatttcgtt tgatgtatga gttttaatga ataaagcgca actacttgtg   1740
catacttgtt gctaatgaaa tgtatcaaaa aaaaaaaaaa aaaaaa               1786
```

<210> SEQ ID NO 6
<211> LENGTH: 499
<212> TYPE: PRT
<213> ORGANISM: Artemisia annua

<400> SEQUENCE: 6

```
Met Ser Ser Gly Ala Asn Gly Ser Ser Lys Ser Ala Ser His Lys Ile
  1               5                  10                  15

Lys Phe Thr Lys Leu Phe Ile Asn Gly Glu Phe Val Asp Ser Ile Ser
             20                  25                  30

Gly Asn Thr Phe Asp Thr Ile Asn Pro Ala Thr Glu Glu Val Leu Ala
         35                  40                  45

Thr Val Ala Glu Gly Arg Lys Glu Asp Ile Asp Leu Ala Val Lys Ala
     50                  55                  60

Ala Arg Glu Ala Phe Asp Asn Gly Pro Trp Pro Arg Met Ser Gly Glu
 65                  70                  75                  80

Ala Arg Arg Lys Ile Met Leu Lys Phe Ala Asp Leu Ile Asp Glu Asn
                 85                  90                  95

Ala Asp Glu Leu Thr Thr Leu Glu Val Ile Asp Gly Gly Lys Leu Phe
            100                 105                 110

Gly Pro Val Arg His Phe Glu Val Pro Val Ser Ser Asp Thr Phe Arg
        115                 120                 125

Tyr Phe Ala Gly Ala Ala Asp Lys Ile Arg Gly Ala Thr Leu Lys Met
    130                 135                 140

Ser Ser Asn Ile Gln Ala Tyr Thr Leu Arg Glu Pro Ile Gly Val Val
145                 150                 155                 160

Gly His Ile Ile Pro Trp Asn Gly Pro Ala Phe Met Phe Ala Thr Lys
                165                 170                 175

Val Ala Pro Ala Leu Ala Ala Gly Cys Thr Met Val Ile Lys Pro Ala
            180                 185                 190

Glu His Thr Pro Leu Thr Val Leu Phe Leu Ala His Leu Ser Lys Leu
        195                 200                 205

Ala Gly Val Pro Asp Gly Val Ile Asn Val Val Asn Gly Phe Gly Lys
    210                 215                 220

Thr Ala Gly Ala Ala Val Ser Ser His Met Asp Ile Asp Met Val Thr
225                 230                 235                 240

Phe Thr Gly Ser Thr Glu Val Gly Arg Thr Val Met Gln Ala Ala Ala
                245                 250                 255

Leu Ser Asn Leu Lys Pro Val Ser Leu Glu Leu Gly Gly Lys Ser Pro
            260                 265                 270

Leu Ile Val Phe Asp Asp Ala Asp Val Asp Lys Ala Ala Glu Phe Ala
        275                 280                 285
```

```
Ile Leu Gly Asn Phe Thr Asn Lys Gly Glu Met Cys Val Ala Gly Ser
    290                 295                 300

Arg Val Phe Val Gln Glu Gly Ile His Asp Val Phe Val Lys Lys Leu
305                 310                 315                 320

Glu Gly Ala Val Lys Ala Trp Ala Thr Arg Asp Pro Phe Asp Leu Ala
                325                 330                 335

Thr Arg His Gly Pro Gln Asn Asn Lys Gln Gln Tyr Asp Lys Val Leu
            340                 345                 350

Ser Cys Ile Asn His Gly Lys Lys Glu Gly Ala Thr Leu Val Thr Gly
        355                 360                 365

Gly Lys Pro Phe Gly Lys Lys Gly Tyr Tyr Ile Glu Pro Thr Leu Phe
    370                 375                 380

Thr Asn Val Thr Asp Asp Met Thr Ile Ala Lys Glu Glu Ile Phe Gly
385                 390                 395                 400

Pro Val Ile Ser Val Leu Lys Phe Lys Thr Val Glu Glu Val Ile Lys
                405                 410                 415

Arg Ala Asn Ala Thr Lys Tyr Gly Leu Ala Ser Gly Val Phe Thr Lys
            420                 425                 430

Asn Ile Asp Val Val Asn Thr Val Ser Arg Ser Ile Arg Ala Gly Ala
        435                 440                 445

Val Trp Val Asn Cys Tyr Leu Ala Leu Asp Arg Asp Ala Pro His Gly
    450                 455                 460

Gly Tyr Lys Met Ser Gly Phe Gly Arg Glu Gln Gly Leu Glu Ala Leu
465                 470                 475                 480

Glu His Tyr Leu Gln Ile Lys Thr Val Ala Thr Pro Ile Tyr Asp Ser
                485                 490                 495

Pro Trp Leu

<210> SEQ ID NO 7
<211> LENGTH: 1584
<212> TYPE: DNA
<213> ORGANISM: Artemisia annua

<400> SEQUENCE: 7
atgtcgtact accatcacca tcaccatcac ctcgaatcaa caagtttgta caaaaaagca      60
ggctccgcgg ccgccccctt caccatgagc tcaggagctc atggaagttc taagtcagca     120
agccataaaa tcaagttcac caagcttttt atcaatggcg aatttgttga ttctatttca     180
ggaaacactt ttgacacgat taatccagcg acagaagaag tgttagcaac agtggccgaa     240
ggaagaaagg aagacattga tttggccgtt aaggctgccc gtgaagcttt cgacaatgga     300
ccttggcctc gcatgtctgg cgaggcacgc cgaaaaatca tgttaaagtt cgcagacttg     360
atcgatgaaa atgctgacga gttaaccacc ttagaagtaa tcgatggagg aaaattgttt     420
ggcccagtga ggcactttga agtcccggtt tcatcagata catttcgtta ctttgcgggt     480
gcagccgata aaatccgtgg agcaactctt aaaatgtcaa gtaatattca agcttatacg     540
ctacgtgaac catcggagt agttggtcac atcattcctt ggaatggtcc tgccttcatg     600
ttcgctacaa aggttgcacc agccttagct gctggctgca ccatggtcat caagcctgcc     660
gaacatactc cccttacagt tctcttttta gctcacctgt cgaagctggc tggtgttcct     720
gatggcgtga ttaatgtggt taacgggttt ggaaaaactg ctggtgctgc cgttagctcg     780
catatggaca ttgacatggt tacttttacg ggatccacag aagttggccg caccgtaatg     840
caagctgcag ctctaagtaa tctgaaacca gtgtcactcg aacttggagg aaaatcgcct     900
```

```
ttgattgttt tcgatgatgc agatgttgat aaagccgcag aatttgctat tttgggaaat    960
tttactaaca aaggtgagat gtgtgtggca gggtctcgtg ttttcgttca ggaagggatc   1020
catgacgtat tcgtaaaaaa attggaagga gcggtgaaag cgtgggcaac aagggaccct   1080
tttgatctcg ccactcgtca tggacctcag aataacaaac aacaatatga taaagtactt   1140
tcatgcatca accatggcaa aaaggaaggt gcgactttgg taaccggtgg taagccattt   1200
gggaagaaag gatactacat tgagcctact ctatttacaa acgttacgga tgatatgacc   1260
atagcaaagg aagaaatttt tggccccgtt atatctgttc tcaagttcaa gactgttgaa   1320
gaagtgatta aaagagcaaa tgccacaaaa tatggacttg cctcaggtgt attcaccaaa   1380
aatattgatg tcgtgaacac agtttcgaga tctattcgag caggtgctgt ttgggtcaac   1440
tgttatttag cactcgaccg ggatgcacct catggagggt ataaaatgag tgggtttgga   1500
cgagaacaag gattagaggc acttgaacat tatcttcaga ttaagacagt ggctacaccc   1560
atatatgatt ccccgtggct ttaa                                         1584
```

<210> SEQ ID NO 8
<211> LENGTH: 527
<212> TYPE: PRT
<213> ORGANISM: Artemisia annua

<400> SEQUENCE: 8

```
Met Ser Tyr Tyr His His His His His His Leu Glu Ser Thr Ser Leu
1               5                   10                  15

Tyr Lys Lys Ala Gly Ser Ala Ala Ala Pro Phe Thr Met Ser Ser Gly
            20                  25                  30

Ala Asn Gly Ser Ser Lys Ser Ala Ser His Lys Ile Lys Phe Thr Lys
        35                  40                  45

Leu Phe Ile Asn Gly Glu Phe Val Asp Ser Ile Ser Gly Asn Thr Phe
    50                  55                  60

Asp Thr Ile Asn Pro Ala Thr Glu Glu Val Leu Ala Thr Val Ala Glu
65                  70                  75                  80

Gly Arg Lys Glu Asp Ile Asp Leu Ala Val Lys Ala Ala Arg Glu Ala
                85                  90                  95

Phe Asp Asn Gly Pro Trp Pro Arg Met Ser Gly Glu Ala Arg Arg Lys
            100                 105                 110

Ile Met Leu Lys Phe Ala Asp Leu Ile Asp Glu Asn Ala Asp Glu Leu
        115                 120                 125

Thr Thr Leu Glu Val Ile Asp Gly Gly Lys Leu Phe Gly Pro Val Arg
    130                 135                 140

His Phe Glu Val Pro Val Ser Ser Asp Thr Phe Arg Tyr Phe Ala Gly
145                 150                 155                 160

Ala Ala Asp Lys Ile Arg Gly Ala Thr Leu Lys Met Ser Ser Asn Ile
                165                 170                 175

Gln Ala Tyr Thr Leu Arg Glu Pro Ile Gly Val Val Gly His Ile Ile
            180                 185                 190

Pro Trp Asn Gly Pro Ala Phe Met Phe Ala Thr Lys Val Ala Pro Ala
        195                 200                 205

Leu Ala Ala Gly Cys Thr Met Val Ile Lys Pro Ala Glu His Thr Pro
    210                 215                 220

Leu Thr Val Leu Phe Leu Ala His Leu Ser Lys Leu Ala Gly Val Pro
225                 230                 235                 240

Asp Gly Val Ile Asn Val Val Asn Gly Phe Gly Lys Thr Ala Gly Ala
                245                 250                 255
```

Ala Val Ser Ser His Met Asp Ile Asp Met Val Thr Phe Thr Gly Ser
            260                 265                 270

Thr Glu Val Gly Arg Thr Val Met Gln Ala Ala Ala Leu Ser Asn Leu
        275                 280                 285

Lys Pro Val Ser Leu Glu Leu Gly Gly Lys Ser Pro Leu Ile Val Phe
290                 295                 300

Asp Asp Ala Asp Val Asp Lys Ala Ala Glu Phe Ala Ile Leu Gly Asn
305                 310                 315                 320

Phe Thr Asn Lys Gly Glu Met Cys Val Ala Gly Ser Arg Val Phe Val
                325                 330                 335

Gln Glu Gly Ile His Asp Val Phe Val Lys Lys Leu Glu Gly Ala Val
            340                 345                 350

Lys Ala Trp Ala Thr Arg Asp Pro Phe Asp Leu Ala Thr Arg His Gly
        355                 360                 365

Pro Gln Asn Asn Lys Gln Gln Tyr Asp Lys Val Leu Ser Cys Ile Asn
    370                 375                 380

His Gly Lys Lys Glu Gly Ala Thr Leu Val Thr Gly Gly Lys Pro Phe
385                 390                 395                 400

Gly Lys Lys Gly Tyr Tyr Ile Glu Pro Thr Leu Phe Thr Asn Val Thr
                405                 410                 415

Asp Asp Met Thr Ile Ala Lys Glu Glu Ile Phe Gly Pro Val Ile Ser
            420                 425                 430

Val Leu Lys Phe Lys Thr Val Glu Glu Val Ile Lys Arg Ala Asn Ala
        435                 440                 445

Thr Lys Tyr Gly Leu Ala Ser Gly Val Phe Thr Lys Asn Ile Asp Val
    450                 455                 460

Val Asn Thr Val Ser Arg Ser Ile Arg Ala Gly Ala Val Trp Val Asn
465                 470                 475                 480

Cys Tyr Leu Ala Leu Asp Arg Asp Ala Pro His Gly Gly Tyr Lys Met
                485                 490                 495

Ser Gly Phe Gly Arg Glu Gln Gly Leu Glu Ala Leu Glu His Tyr Leu
            500                 505                 510

Gln Ile Lys Thr Val Ala Thr Pro Ile Tyr Asp Ser Pro Trp Leu
        515                 520                 525

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
caccatggaa cagcaacaag aag                                    23

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
tcattcatgc gcaaccacca cca                                    23

<210> SEQ ID NO 11
<211> LENGTH: 22
<212> TYPE: DNA
<213> ORGANISM: Artificial Sequence

```
<220> FEATURE:
<223> OTHER INFORMATION: Synthetic primer

<400> SEQUENCE: 11
caccatgagc tcaggagcta at                                          22

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
ttaaagccac ggggaatcat at                                          22

<210> SEQ ID NO 13
<211> LENGTH: 6
<212> TYPE: PRT
<213> ORGANISM: Artificial Sequence
<220> FEATURE:
<223> OTHER INFORMATION: Synthetic 6x His tag

<400> SEQUENCE: 13

His His His His His His
1               5
```